United States Patent
Prud'Homme et al.

(10) Patent No.: US 11,103,461 B2
(45) Date of Patent: Aug. 31, 2021

(54) PROCESS FOR ENCAPSULATING SOLUBLE BIOLOGICS, THERAPEUTICS, AND IMAGING AGENTS

(71) Applicant: The Trustees of Princeton University, Princeton, NJ (US)

(72) Inventors: Robert K. Prud'Homme, Princeton, NJ (US); Robert F. Pagels, Princeton, NJ (US); Chester E. Markwalter, Princeton, NJ (US)

(73) Assignee: THE TRUSTEES OF PRINCETON UNIVERSITY, Princeton, NJ (US)

(*) Notice: Subject to any disclaimer, the term of this patent is extended or adjusted under 35 U.S.C. 154(b) by 0 days.

(21) Appl. No.: 16/064,935

(22) PCT Filed: Dec. 21, 2016

(86) PCT No.: PCT/US2016/068145
§ 371 (c)(1),
(2) Date: Jun. 21, 2018

(87) PCT Pub. No.: WO2017/112828
PCT Pub. Date: Jun. 29, 2017

(65) Prior Publication Data
US 2019/0008788 A1 Jan. 10, 2019

Related U.S. Application Data

(60) Provisional application No. 62/387,075, filed on Dec. 22, 2015.

(51) Int. Cl.
| | | |
|---|---|---|
| *A61K 9/50* | (2006.01) | |
| *B01J 13/06* | (2006.01) | |
| *A61K 9/16* | (2006.01) | |
| *A61K 9/51* | (2006.01) | |
| *A61K 9/00* | (2006.01) | |

(52) U.S. Cl.
CPC .......... *A61K 9/5089* (2013.01); *A61K 9/1647* (2013.01); *A61K 9/5026* (2013.01); *A61K 9/5031* (2013.01); *A61K 9/5138* (2013.01); *A61K 9/5146* (2013.01); *A61K 9/5153* (2013.01); *A61K 9/5192* (2013.01); *B01J 13/06* (2013.01); *A61K 9/0019* (2013.01)

(58) Field of Classification Search
CPC .. A61K 9/0019; A61K 9/1647; A61K 9/5026; A61K 9/5031; A61K 9/5089; A61K 9/5138; A61K 9/5146; A61K 9/5153; A61K 9/5192; B01J 13/06
See application file for complete search history.

(56) References Cited

U.S. PATENT DOCUMENTS

| | | | |
|---|---|---|---|
| 4,342,653 A | 8/1982 | Halverson | |
| 4,382,982 A | 5/1983 | Whillans | |
| 4,999,417 A | 3/1991 | Domb | |
| 5,366,734 A | 11/1994 | Hutchinson | |
| 5,578,325 A | 11/1996 | Domb et al. | |
| 6,291,013 B1 | 9/2001 | Gibson et al. | |
| 6,383,500 B1 | 5/2002 | Wooley et al. | |
| 6,730,322 B1 | 5/2004 | Bernstein et al. | |
| 7,977,024 B2 | 7/2011 | Zhou et al. | |
| 8,137,699 B2 | 3/2012 | Johnson et al. | |
| 8,288,001 B1 | 10/2012 | Fan et al. | |
| 9,782,358 B2* | 10/2017 | Kataoka | A61P 43/00 |
| 10,231,937 B2* | 3/2019 | Pagels | A61K 38/063 |
| 2004/0091546 A1 | 5/2004 | Johnson et al. | |
| 2004/0236050 A1 | 11/2004 | Lundquist et al. | |
| 2005/0158390 A1 | 7/2005 | Rana et al. | |
| 2005/0228074 A1 | 10/2005 | Warren et al. | |
| 2006/0057215 A1 | 3/2006 | Raiche et al. | |
| 2006/0078624 A1 | 4/2006 | Zalipsky et al. | |
| 2006/0159921 A1* | 7/2006 | Murthy | B01J 13/02 428/402 |
| 2006/0224095 A1 | 10/2006 | Claverie et al. | |
| 2006/0247383 A1 | 11/2006 | Hedrick et al. | |
| 2007/0231355 A1 | 10/2007 | Quadir et al. | |
| 2008/0145432 A1 | 6/2008 | Kakizawa et al. | |
| 2008/0160305 A1 | 7/2008 | Warren et al. | |
| 2009/0061009 A1 | 3/2009 | Schwarz et al. | |
| 2009/0325292 A1 | 12/2009 | Baker et al. | |
| 2010/0150994 A1 | 6/2010 | Kotyla | |

(Continued)

FOREIGN PATENT DOCUMENTS

| | | |
|---|---|---|
| CN | 102334609 A | 2/2012 |
| CN | 104042567 A | 9/2014 |

(Continued)

OTHER PUBLICATIONS

Pagels et al., "Polymeric Nanoparticles and Microparticles for the Delivery of Peptides, Biologics, and Soluble Therapeutics." J. Controlled Release; vol. 219; pp. 519-535; published online Sep. 8, 2015.*
Six IQQueryQuickExport search results (IP.com NPL search results)—downloaded Apr. 30, 2020.*
Google Scholar NPL search string—downloaded Apr. 29, 2020.*
Anton et al.; Langmuir 2009 25(19), pp. 11413-11419. Published online Jul. 16, 2009.*
Int'l Search Report and Written Opinion dated Sep. 18, 2015 in Int'l Application PCT/US2015/036060.
Bronich et al., "Polymer Micelle with Cross-Linked Ionic Core" J. Am. Chem Soc., 127, pp. 8236-8237, 2005.
Arshady, "Preparation of biodegradable microspheres and microcapsules: 2. Polyactides and related polyesters", Journal of Controlled Release, 17, pp. 1-22, 1991.
Holland et al., "Polymers for Biodegradable Medical Devices, 1. The Potential of Polyesters as Controlled by Macromolecular Release Systems", Journal of Controlled Release, 4, pp. 155-180, 1986.

(Continued)

*Primary Examiner* — Jeffrey T. Palenik
(74) *Attorney, Agent, or Firm* — Panitch Schwarze Belisario & Nadel LLP; Lars H. Genieser

(57) ABSTRACT

An "inverse" precipitation route to precipitate aqueous soluble species with copolymers as nanoparticles having a hydrophilic, polar core and a less polar shell is described. The aggregation of these nanoparticles to form larger microparticles and monoliths provides a highly loaded construct (e.g., a depot) for the sustained and controlled release of actives.

45 Claims, 10 Drawing Sheets

(56) References Cited

U.S. PATENT DOCUMENTS

| | | |
|---|---|---|
| 2010/0233251 A1 | 9/2010 | Von Andrian et al. |
| 2010/0305219 A1 | 12/2010 | Granick et al. |
| 2010/0310649 A1 | 12/2010 | Richard et al. |
| 2010/0330368 A1 | 12/2010 | Prud'homme et al. |
| 2011/0012057 A1 | 1/2011 | Lindner et al. |
| 2011/0022129 A1 | 1/2011 | Prud'homme et al. |
| 2011/0200828 A1 | 8/2011 | Li et al. |
| 2011/0236686 A1 | 9/2011 | Kitano et al. |
| 2011/0293701 A1 | 12/2011 | Bratzler et al. |
| 2012/0009267 A1 | 1/2012 | Cho et al. |
| 2012/0041150 A1 | 2/2012 | Yabu et al. |
| 2012/0171254 A1 | 7/2012 | Johnson et al. |
| 2012/0230913 A1 | 9/2012 | Johnston et al. |
| 2012/0308640 A1 | 12/2012 | Percec et al. |
| 2013/0101516 A1 | 4/2013 | Zhao |
| 2013/0122058 A1 | 5/2013 | Chow et al. |
| 2013/0171208 A1 | 7/2013 | Smith et al. |
| 2013/0337078 A1 | 12/2013 | Mayer et al. |
| 2014/0037573 A1 | 2/2014 | Eliasof et al. |
| 2014/0099379 A1 | 4/2014 | Beck-Broichsitter et al. |
| 2014/0249235 A1 | 9/2014 | Brugel et al. |
| 2014/0356443 A1 | 12/2014 | Brisander et al. |
| 2015/0283218 A1 | 10/2015 | Shea et al. |
| 2015/0299369 A1 | 10/2015 | Ausserre et al. |
| 2016/0346266 A1 | 12/2016 | Tolleth et al. |
| 2017/0042823 A1 | 2/2017 | Prud'Homme et al. |
| 2019/0008788 A1 | 1/2019 | Prud'Homme et al. |

FOREIGN PATENT DOCUMENTS

| | | |
|---|---|---|
| EP | 2962752 A1 | 1/2016 |
| JP | 2008297288 A | 12/2008 |
| JP | 2014514275 A | 6/2014 |
| JP | 2015129128 A | 7/2015 |
| WO | 1997049736 A2 | 12/1997 |
| WO | 2002076441 A1 | 10/2002 |
| WO | 2002078674 A1 | 10/2002 |
| WO | 2009080164 | 7/2009 |
| WO | 2012122544 A2 | 9/2012 |
| WO | 2013023003 A1 | 2/2013 |
| WO | 2013160773 A2 | 10/2013 |
| WO | 2014133172 A1 | 9/2014 |
| WO | 2014165679 A1 | 10/2014 |
| WO | 2015130835 A1 | 9/2015 |
| WO | 2015200054 A2 | 12/2015 |
| WO | 2017112828 A1 | 6/2017 |

OTHER PUBLICATIONS

Lavasanifar et al., Poly(ethylene oxide)-block-poly(L-amino acid) micelles for drug delivery, Advanced Drug Delivery Reviews, 54, pp. 169-190, 2002.

Liu et al., "CFD Predictions for Chemical Processing in a Confined Impinging-Jets Reactor" AIChE Journal, vol. 52, No. 2, pp. 731-744, Feb. 2006.

Pitt, "The controlled parenteral delivery of polypeptides and proteins", International Journal of Pharmaceutics, 59, pp. 173-196, 1990.

Bontha et al., "Polymer micelles with cross-linked ionic cores for delivery of anticancer drugs", Journal of Controlled Release, 114, pp. 163-174, 2006.

Zhang et al., "Amphiphilic cylindrical brushes with poly(acrylic acid) core and poly(n-butyl acrylate) shell and narrow ength distribution", Polymer, 44, pp. 1449-1458, 2003.

Sato et al., "Therapeutic peptides: technological advances driving peptides into development", Current Opinion in Biotechnology, 17, pp. 638-642, 2006.

Peters et al., "Biotech Products in Big Pharma Clinical Pipelines Have Grown Dramatically According to the Tufts Center for the Study of Drug Development", Nov. 14, 2013, https://www.biospace.com/...a-clinical-pipelines-have-grown-dramatically-according-to-the-tufts-center-for-the-study-of-drug-development-/, accessed Aug. 29, 2018 (5 pages).

Liu et al., "Mixing in a multi-inlet vortex mixer (MIVM) for flash nano-precipitation", Chemical Engineering Science, 63, pp. 2829-2842, 2008.

Mitragotri et al. "Overcoming the challenges in administering biopharmaceuticals: formulation and delivery strategies" Nat Rev Drug Discov., 13(9): 655-672, Sep. 2014.

Patil et al., "Retention of trypsin activity in spermine alginate microcapsules", Journal of Microencapsulation, vol. 14, No. 4, pp. 469-474, 1997.

Bronich et al., "Soluble Complexes from Poly(ethylene oxide)-block-polymethacrylate Anions and N-Alkylpyridinium Cations", Macromolecules, vol. 30, pp. 3519-3525, 1997.

Bilati et al., "Nanoprecipitation Versus Emulsion-based Techniques for the Encapsulation of Proteins Into Biodegradable Nanoparticles and Process-related Stability Issues", AAPS PharmSciTech, vol. 6, No. 4, Article 74, pp. E594-E604, 2005.

Extended European Search Report (EESR) dated Jan. 8, 2018 in European Application No. 15811879.4.

Kakizawa et al., "Controlled release of protein drugs from newly developed amphiphilic polymer-based microparticles composed of nanoparticles", Journal of Controlled Release, 142, pp. 8-13, 2010.

D'Addio et al., "Controlling drug nanoparticle formation by rapid precipitation", Advanced Drug Delivery Reviews, 63, pp. 417-426, 2011.

Okuyama et al., "Preparation of functional nanostructured particles by spray drying", Advanced Powder Technol., vol. 17, No. 6, pp. 587-611, 2006.

O'Reilly et al., "Cross-linked block copolymer micelles: funtional nanostructures of great potential and versatility", Chemical Society Reviews, 35, pp. 1068-1083, 2006.

Johnson et al., "Characterization and Suitability of Therapeutic Antibody Dense Phases for Subcutaneous Delivery", Molecular Pharmaceutics, 10, pp. 3582-3591, 2013.

Johnston et al., "Concentrated Dispersions of Equilibrium Protein Nanoclusters That Reversibly Dissociate into Active Monomers", ACS Nano, vol. 6, No. 2, pp. 1357-1369, 2012.

Johnson et al. "Chemical Processing and Micromixing in Confined Impinging Jets", AiChE Journal, vol. 49, No. 9, pp. 2264-2282, 2003.

Int'l Search Report and Written Opinion dated Jul. 16, 2015 in Int'l Application No. PCT/US2015/017590.

Int'l Search Report and Written Opinion dated Mar. 23, 2017 in Int'l Applicaiton No. PCT/US2016/068145.

Bilati et al., Development of a nanoprecipitation method intended for the entrapment of hydrophilic drugs into nanoparticles, European J. Pharmaceutical Sciences, vol. 24, pp. 67-75 (2005).

Gao et al., Core Cross-Linked Reverse Micelles from Star-Shaped Polymers, Chemistry of Materials, vol. 20, pp. 3063-3067 (2008).

Int'l Search Report and Written Opinion dated Mar. 23, 2017 in Int'l Application No. PCT/US2016/068145.

Liang et al., Preparation of nanoparticles composed of poly(gamma-glutamic acid)-poly(lactide) block copolymers and avaluation of their uptake by HepG2 cells, J. Controlled Release, vol. 105, pp. 213-225 (2005).

Pustulka et al., Flash Nanoprecipitation: Particle Structure and Stability, Molecular Pharmaceutics, vol. 10, pp. 4367-4377 (2013).

Zandonella, "Bob Prud'homme—Flash NanoPrecipitation" http://research.princeton.edu/news/features/a/index.xml?id=6234, accessed Mar. 9, 2018, originally published Dec. 9, 2011, 2 printed pages.

Zhu et al., Preparation and characterization of hCG-loaded polylactide or poly(lactide-co-glycolide) microspheres using a modified water-in-oil-in-water (w/o/w) emulsion solvent evaporation technique, J. Microencapsulation, vol. 18, No. 2, op. 247-260 (2001).

U.S. Appl. No. 15/321,588 Notice of Allowance dated Oct. 24, 2018.

U.S. Appl. No. 15/321,588 Summary of Examiner Interview dated Oct. 9, 2018.

U.S. Appl. No. 15/321,588 Office Action dated Apr. 10, 2018.

U.S. Appl. No. 15/321,588 Restriction Requirement dated Dec. 1, 2017.

U.S. Appl. No. 16/253,850 Restriction Requirement dated Apr. 7, 2020.

(56) References Cited

OTHER PUBLICATIONS

Deng et al., "Janus Nanoparticles of Block Copolymers by Emulsion Solvent Evaporation Induced Assembly", Macromolecules, vol. 49, pp. 1362-1368 (2016).
Foerster et al., "Amphiphilic Block Copolymers in Structure-Controlled Nanomaterial Hybrids", Advanced Materials, vol. 10, No. 3, pp. 195-217 (1998).
Groeschel et al., "Guided hierarchical co-assembly of soft patchy nanoparticles". Nature, vol. 503, pp. 247-251 (5 pages & 11 pages Methods, Extended Data Figures 1-9, & Extended Data Table 1) (Nov. 14, 2013).
Guo et al., "Binding of dihydromyricetin and its metal ion complexes with bovine serum albumin", Biotechnology & Biotechnological Equipment, vol. 28, No. 2, pp. 333-341 (2014).
Guo et al., "Synthesis of dihydromyricetin-manganese (II) complex and interaction with DNA", J. Molecular Structure, vol. 1027, pp. 64-69 (2012).
International Search Report and Written Opinion dated Dec. 6, 2018 in International Application No. PCT/US2018/050714.
International Search Report and Written Opinion dated Jan. 15, 2019 in International Application No. PCT/US2018/049580.
International Search Report and Written Opinion dated Feb. 22, 2019 in International Application No. PCT/US2018/058869.
International Search Report and Written Opinion dated Nov. 22, 2019 in International Application No. PCT/US2019/042574.
International Search Report and Written Opinion dated Jan. 26, 2018 in International Application No. PCT/US2017/054779.
Jang et al., "Bicontinuous Block Copolymer Morphologies Produced by Interfacially Active, Thermally Stable Nanoparticles", Macromols., vol. 44, pp. 9366-9373 (2011).
Jang et al., "Synthesis of thermally stable Au-core/Pt-shell nanoparticles and their segregation behavior in diblock copolymer mixtures", Soft Matter, vol. 7, pp. 6255-6263 (2011), doi: 10.1039/clsm05223c.
Jeon et al., "Cooperative Assembly of Block Copolymers with Deformable Interfaces: Toward Nanostructured Particles", Advanced Materials, vol. 20, pp. 4103-4108 (2008), doi: 10.1002/adma. 200801377.
Johnson et al., "Nanoprecipitation of organic actives using mixing and block copolymer stabilization", Abstracts of Papers of the American Chemical Society, No. 186 (Abstract) (Sep. 2003).
Kang et al., "Pore Closing and Opening in Biodegradable Polymers and Their Effect on the Controlled Release of Proteins", Mol. Pharmaceutics, vol. 4, No. 1, pp. 104-118 (2007).
Kim et al., "Critical effect of freezing/freeze-drying on sustained release of FITC-dextran encapsulated within PLGA microspheres", Int'l J. Pharmaceutics, vol. 271, pp. 207-214 (2004).
Kumar et al., "Amphiphilic Janus particles at fluid interfaces", Soft Matter, vol. 9, pp. 6604-6617 (2013).
Liu et al., "Janus Colloids Formed by Biphasic Grafting at a Pickering Emulsion Interface", Angew. Chern., vol. 120, pp. 4037-4039 (2008).
Mai et al., "Controlled Incorporation of Particles into the Central Portion of Vesicle Walls", J. Am. Chem. Soc., vol. 132, pp. 10078-10084 (2010).

Riess et al., "Emulsifying Properties of Block Copolymers. Oil-Water Emulsions and Microemulsions", Polym. Eng. Sci., vol. 17, No. 8, pp. 634-638 (1977).
Saad et al., "Principles of nanoparticle formation by Flash Nanoprecipitation", Nano Today, vol. 11, No. 2, pp. 212-227 (2016), http://dx.doi.org/10.1016/j.nantod.2016.04.006.
Sahoo et al., "Characterization of Porous PLGA/PLA Microparticles as a Scaffold for Three Dimensional Growth of Breast Cancer Cells", Biomacromolecules, vol. 6, pp. 1132-1139 (2005).
Solaro et al., "Targeted Delivery of Protein Drugs by Nanocarriers", Materials, vol. 3, pp. 1928-1980 (2010).
Sosa et al., "Soft Multifaced and Patch Colloids by Constrained Volume Self-Assembly", Macromolecules, vol. 49, pp. 3580-3585 (2016).
Steichen et al., "A review of current nanoparticle and targeting moieties for the delivery of cancer therapeutics", European J. Pharmaceutical Sciences, vol. 48, pp. 416-427 (2013).
Wang et al., "Characterization of the initial burst release of a model peptide from poly(D,L-lactide-co-glycolide) microspheres", J. Conlrolled Release, vol. 82, pp. 289-307 (2002).
Xu et al., "Scalable method to produce biodegradable nanoparticles that rapidly penetrate human mucus", Journal of Controlled Release, vol. 170, pp. 279-286 (2013).
Colombani et al., "Structure of Micelles of Poly(n-butyl acrylate)-block-poly(acrylic acid) Diblock Copolymers in Aqueous Solution," Macromolecules, vol. 40, pp. 4351-4362 (2007).
Colombani et al., "Synthesis of Poly(n-butyl acrylate)-block-poly(acrylic acid) Diblock Copolymers by ATRP and Their Micellization in Water," Macromolecules, vol. 40, pp. 4338-4350 (2007).
Eghbali et al., "Rheology and Phase Behavior of Poly(n-butyl acrylate)-block-poly(acrylic acid) in Aqueous Solution," Langmuir, vol. 22, pp. 4766-4776 (2006).
Erre et al., "Chromium(lll) Acetate, Chromium(lll) Acetate Hydroxide, or u3-0xo-esakis-(u2-acetato-O,O')-triaqua-trichromium(lll) Acetate?" Journal of Chemical Education, vol. 74, No. 4, pp. 432-435 (1997).
Kim et al., "Multicomponent Nanoparticles via Self-Assembly with Cross-Linked Block Copolymer Surfactants," Langmuir, vol. 23, pp. 2198-2202 (2007).
Kohen, N., "Characterization of Polystyrene-block-poly(acrylic acid) Micelles in Solution and Assembled on Solid Substrates," Massachusetts Institute of Technology, Thesis, Jun. 2005, pp. 1-38 (2005).
Qi et al., "Determination of the Bioavailability of Biotin Conjugated onto Shell Cross-Linked (SCK) Nanoparticles," Journal of the American Chemical Society, vol. 126, pp. 6599-6607 (2004).
U.S. Appl. No. 16/253,850 Office Action dated Sep. 8, 2020.
Talelli et al., "Core-crosslinked polymeric micelles: Principles, preparation, biomedical applications and clinical translation," Nano Today, vol. 10, pp. 93-117 (2015).
U.S. Patent & Trademark Office (USPTO) Communication dated Mar. 9, 2021 for U.S. Appl. No. 16/253,850.
U.S. Patent & Trademark Office (USPTO) Office Action dated May 12, 2021 for U.S. Appl. No. 16/810,710.

* cited by examiner

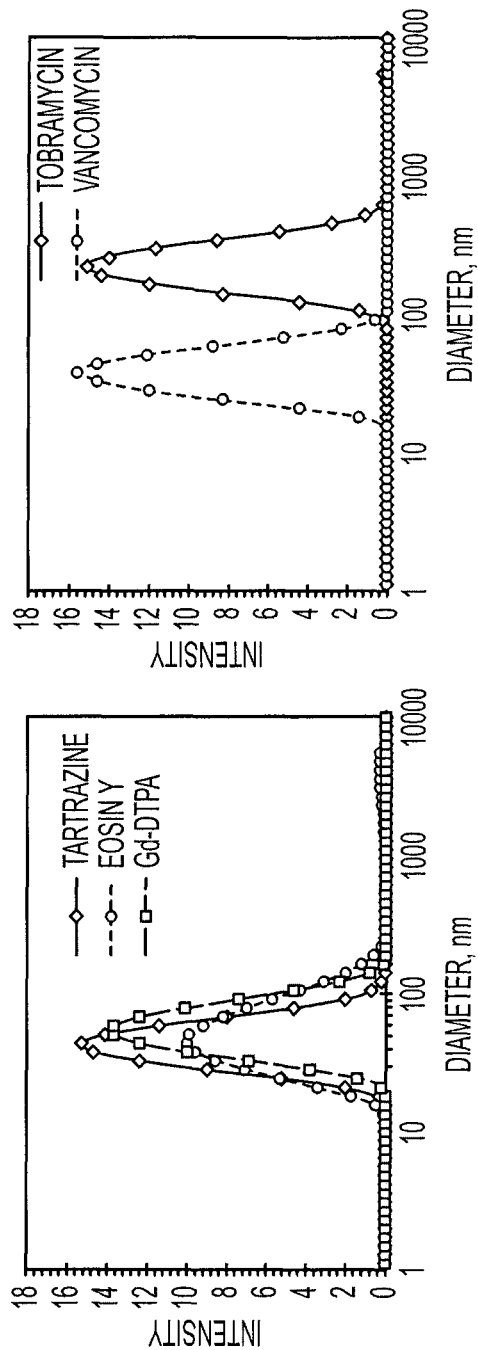

PROCESS FOR ENCAPSULATING SOLUBLE BIOLOGICS, THERAPEUTICS, AND IMAGING AGENTS

This application claims the benefit of U.S. Provisional Application No. 62/387,075, filed Dec. 22, 2015, the specification of which is hereby incorporated by reference in its entirety.

FIELD OF THE INVENTION

The present invention relates to a process of making microparticles comprising aggregated nanoparticles having a hydrophilic core.

BACKGROUND OF THE INVENTION

Protein and peptide therapeutics are a growing segment of the pharmaceutical marketplace. In eleven years, from 2001 to 2012, the global sales of pharmaceutical biologic therapeutics (biologics) more than tripled from $36 billion to $163 billion. In that same period, revenue generated by biologics within the top 10 selling pharmaceuticals increased from 7% to 71% (S. Peters, Biotech Products in Big Pharma Clinical Pipelines Have Grown Dramatically, Tufts CSDD Impact Report. 15 (2013) 1). Their specificity makes them ideal therapeutics for the treatment of a variety of diseases including cancer and AIDS. This specificity comes as a result of structural complexity, which is a strength of biologics for use as therapeutics and a challenge in trying to formulate and deliver them (S. Mitragotri, P. A. Burke, R. Langer, Overcoming the challenges in administering biopharmaceuticals: formulation and delivery strategies, Nat Rev Drug Discov. 13 (2014) 655-672).

While humanized antibodies may be long circulating, proteins and peptides can be cleared from the bloodstream in a matter of minutes either due to renal clearance or enzymatic degradation (A. K. Sato, M. Viswanathan, R. B. Kent, C. R. Wood, Therapeutic peptides: technological advances driving peptides into development, Curr. Opin. Biotechnol. 17 (2006) 638-642). Therefore, delivery and extended release can require encapsulation of the biologic into nanoparticles (NPs) and microparticles (MPs). NPs can be defined as having sizes below 400 nm, making them prospects for injectable formulations, and MPs can be defined as having sizes above 1-10 microns, so that they are appropriate for depot delivery. Requirements of NPs and MPs are high loading, high encapsulation efficiency, and an appropriate release profile of the biologic therapeutic. These particles are commonly delivered parenterally. While there have been recent promising advances in oral delivery of biologics, the difficulty in translocating NPs through mucus layers and across the GI (gastrointestinal) tract epithelial layer makes this a less developed area than parenteral administration. However, the principles for NP formulation apply equally to oral or parenteral NPs. Examples of carriers include hydrogel carriers composed of water soluble polymers and non-swellable carriers composed of hydrophobic or solid matrices.

The term "biologic" can encompass a range of therapeutics including peptides, oligonucleotides, polypeptides, polypeptide antibiotics, proteins, and antibodies. For example, a peptide may include a sequence of 1 to 40 amino acids. In an expanded use within this document, the term "biologic" is also used to refer to any water soluble molecules including dyes and small molecule saccharides which may also be used in this invention.

SUMMARY

A method of the invention for encapsulating water soluble molecules using rapid, controlled precipitation is presented. Water soluble molecules—including peptides, proteins, DNA, RNA, non-biologic therapeutics, polysaccharide-based therapeutics (e.g., tobramycin) and imaging agents—precipitate into nanoparticles that are protected by a copolymer stabilizing agent. These particles may be covalently or non-covalently stabilized. The particles thus made are colloidally stable in the first nonpolar solvent phase. The particles can be subsequently processed in such a manner to make an aggregate of the nanoparticles, called a microparticle. The microparticles can have weight-average sizes from 1 micron to 1 mm or 2 mm. The aggregation process may involve spray drying of the original stable dispersion to cause aggregation. Alternatively, the aggregation process can involve an emulsification step into a polar solvent, followed by the removal of the nonpolar solvent to solidify the microparticle. Dispersants may be added to the formulation during the emulsification step to minimize microparticle interactions.

The invention of this microparticle processes overcomes limitations of current processes for making microparticles. Those processes are commonly based on water-in-oil-in-water (w/o/w) emulsification processes. In these processes, rather than a precipitation of the soluble agent as described herein, the agent is solubilized in a polar solvent which emulsified in a nonmiscible external nonpolar oil phase. This first emulsion is then dispersed in a second polar aqueous phase and the nonpolar solvent removed. The lack of control in the emulsion step and the fact that the internal soluble drop is a fluid has limited loadings that can be achieved and controlled release kinetics to microparticles with loadings generally less than 10 wt % solids. These processes and their limitations have been discussed in a review article (J. Controlled Release. 219 (2015) 519-535), which is included in its entirety. Secondarily, the previous w/o/w processes relied upon the matrix of the microparticle, which is generally polylactic-co-glycolic acid polymer to control release. The lack of uniformity of those coatings, again, compromises release control at high agent loadings. In sharp contrast, the amphiphilic copolymer coating that encapsulates each nanoparticle in the current invention, for example, the (e.g., hydrophobic) portion of the amphiphilic copolymer that forms the shell can largely control release, rather than the matrix. That enables more precise control of release rates from each nanoparticle, and enables microparticle formation with no added matrix, or a minor amount of matrix material so that higher agent loadings can be achieved than have been achieved in previous w/o/w formulations. Additionally, the initial nanoparticle formation step in the current invention allows for fine dispersions of the biologic throughout the microparticle, which is difficult to achieve in the w/o/w emulsion process and has been shown to be important for prolonged, controlled release. Loading of up to 25 wt %, 50 wt %, 66 wt %, 75 wt %, to 80 wt % can be achieved, with controlled release profiles. The combination of high loading, lack of burst release, and controlled release in microparticles from 1 micron to 1 mm or 2 mm constructs has not been possible previously.

Previous attempts to make microparticles from dried actives, to avoid the two-emulsions steps, have been reviewed in an article (J Controlled Release. 219 (2015)

519-535). These approaches fail because the dry agent powders cannot be commuted down to nanoparticle size. Therefore, in the emulsion step with these powders to make microparticles, particle contacts cause percolation and lack of controlled release when formulations of high active loading are attempted.

In the current invention, the biologic is first formulated into nanoparticles sterically stabilized in a non-polar organic solvent by an amphiphilic polymer. The nanoparticles are composed of a hydrophilic core containing the biologic and the hydrophilic regions of the stabilizing polymer, and a hydrophobic shell composed of the hydrophobic regions of the stabilizing polymer. These nanoparticles may be coated with an amphiphilic polymer, or processed into microparticles or larger monoliths. Post processing on the final construct may be conducted. Because these nanoparticles have a hydrophilic core and a hydrophobic shell, they may be termed "inverse nanoparticles" (however, at times, these nanoparticles may be simply referred to as "nanoparticles").

A method of the invention for encapsulating a water soluble agent includes dissolving the water soluble agent and a copolymer in a polar process solvent to form a first process solution. Alternatively, the water soluble agent may be dissolved in a first polar process solvent to form a water soluble agent solution, and the copolymer may be dissolved in a second polar process solvent to form a copolymer solution. That is, a method of the invention includes dissolving the water soluble agent in a polar process solvent stream and the copolymer in a separate polar solvent stream. The first polar process solvent and the second polar process solvent may be the same or different. The first process solution (or the water soluble agent solution and the copolymer solution) can be continuously mixed with a nonprocess solvent to form a mixed solution from which a nanoparticle ("inverse nanoparticle") assembles and precipitates. The multiple polar process solutions can be continuously mixed with a nonprocess solvent as described above. The copolymer can include at least one region that is more polar and at least one region that is less polar. The nonprocess solvent is or can be less polar than the polar process solvent. The nanoparticle can include a core and a shell. The core can include the more polar region of the copolymer and the water soluble agent. The shell can include the less polar region of the copolymer. The mixing can cause no more than 20 percent by volume of the polar process solvent to phase separate.

In a method of the invention, the water soluble agent can be a biologic material, an amino acid, a peptide, a protein, DNA, RNA, a saccharide, glutathione, tryptophan, a lysozyme, glucagon-like peptide-1 (GLP-1), a small molecule therapeutic, tobramycin, vancomycin, an imaging agent, eosin Y, tartrazine, a metal chelate, a gadolinium chelate, gadolinium diethylene triamine pentaacetic acid (GD-DTPA), or combinations.

For example, the copolymer can be a random copolymer, a block copolymer, a diblock copolymer, a triblock copolymer, a multiblock copolymer, or a branched-comb copolymer. For example, the copolymer can include at least one more polar region (region that is more polar). The at least one more polar region of the copolymer can include at least one anionic more polar region. For example, this anionic more polar region can include anionic residues (units or monomers), poly(acrylic acid) (PAA), hyaluronic acid, poly (glutamic acid), poly(aspartic acid), or combinations.

For example, the at least one more polar region of the copolymer can include at least one cationic more polar region. For example, this cationic more polar region may include cationic residues, such as chitosan polymer domains, histadine lipids, histamines, spermadines, polyethylene-imines, or combinations.

For example, the copolymer can include at least one less polar region (region that is less polar) that includes poly(n-butyl acrylate) (PBA), poly(lactic acid) (PLA), poly(caprolactone) (PCL), poly(lactic-co-glycolic acid) (PLGA), poly (propylene sulfide), polyanhydrides, lipid or phospholipid grafted units, or cholesterol grafted units, or combinations. For example, the copolymer can be poly(acrylic acid)-block-poly(n-butyl acrylate) (PAA-b-PBA).

In a method of the invention, the polar process solvent can be water, an alcohol, methanol, ethanol, acetone, acetonitrile, glycol ethers, dimethyl sulfoxide (DMSO), dimethylformamide (DMF), N-methyl pyrrolidone (NMP), or combinations. Glycol ethers include: ethylene glycol monomethyl ether (2-methoxyethanol, $CH_3OCH_2CH_2OH$), ethylene glycol monoethyl ether (2-ethoxyethanol, $CH_3CH_2OCH_2CH_2OH$), ethylene glycol monopropyl ether (2-propoxyethanol, $CH_3CH_2CH_2OCH_2CH_2OH$), ethylene glycol monoisopropyl ether (2-isopropoxyethanol, $(CH_3)_2CHOCH_2CH_2OH$), ethylene glycol monobutyl ether (2-butoxyethanol, $CH_3CH_2CH_2CH_2OCH_2CH_2OH$), ethylene glycol monophenyl ether (2-phenoxyethanol, $C_6H_5OCH_2CH_2OH$), ethylene glycol monobenzyl ether (2-benzyloxyethanol, $C_6H_5CH_2OCH_2CH_2OH$), diethylene glycol monomethyl ether (2-(2-methoxyethoxy)ethanol, methyl carbitol, $CH_3OCH_2CH_2OCH_2CH_2OH$), DEG monobutyl ether (2-(2-ethoxyethoxy)ethanol, butyl carbitol, $CH_3CH_2OCH_2CH_2OCH_2CH_2OH$), diethylene glycol monoethyl ether (2-(2-ethoxyethoxy)ethanol, carbitol cellosolve, $CH_3CH_2OCH_2CH_2OCH_2CH_2OH$), and diethylene glycol mono-n-butyl ether (2-(2-butoxyethoxy)ethanol, $CH_3CH_2CH_2CH_2OCH_2CH_2OCH_2CH_2OH$)

In a method of the invention there may be more than one polar process solvent used.

In a method of the invention, the nonprocess solvent can be chloroform, dichloromethane, an alkane, hexane, an ether, diethyl ether, tetrahydrofuran (THF), toluene, acetone, or combinations. For example, the nonprocess solvent can be chloroform, acetone, or combinations. For example, the polar process solvent and the nonprocess solvent can be miscible. In the preferred embodiment, the process and nonprocess solvents are completely miscible at the volume ratios used in the nanoparticle formation process. Alternately, in another embodiment, the process solvent is substantially soluble in the nonprocess solvent, where substantially soluble is defined as having 80% by volume of the process solvent miscible in the nonprocess solvent under volume ratios used in the nanoparticle formation process.

In a method of the invention, a time of mixing of the process solution with the nonprocess solvent is less than an assembly time of the nanoparticle. For example, the water soluble agent and the copolymer can have a supersaturation level in the solution ranging from 10 to 10,000. For example, the nanoparticle can have a size ranging from about 40 nm to about 400 nm. For example, the nanoparticle can have a size ranging from about 40 nm to about 900 nm.

A method of the invention includes stabilizing the nanoparticle core through crosslinking of the copolymer. For example, the nanoparticle can be crosslinked during assembly of the nanoparticle. For example, the nanoparticle can be crosslinked after assembly of the nanoparticle. The crosslinking can be covalent crosslinking. For example, the crosslinking can be disulfide crosslinking. The crosslinking can involve as cleavable ester linkage of the types described in U.S. patent application Ser. No. 13/969,449, Particulate Constructs for Release of Active Agents, Lawrence Mayer, et al. The crosslinking can be non-covalent. For example the crosslinking can be ionic, chelation, acid-base, or hydrogen bonding crosslinking.

A crosslinking agent can be added to crosslink the copolymer. For example, the crosslinking agent can be added to crosslink a portion of the copolymer of anionic functionality. For example, the crosslinking agent can be an alkaline earth halide, a magnesium halide, magnesium chloride, a calcium halide, calcium chloride, a transition metal halide, an iron halide, iron(III) chloride, spermine, or combinations. For example, the crosslinking agent can be a metal acetate, an alkaline earth acetate, a transition metal acetate, calcium acetate, or combinations. For example, the crosslinking agent can be chromium(III) acetate, or another chromium (III) salt. For example, the water soluble agent can include tobramycin and the tobramycin can crosslink the copolymer. Other bio-compatible multi-cationic water soluble agents may be used as crosslinking agents, for example, to crosslink anionic sections of the copolymer.

If the polar agent includes cationic functional groups, then crosslinking may be achieved by the addition of polyanionic components. Examples of these are poly(acrylic acid) (PAA), hyaluronic acid, poly(glutamic acid), poly (aspartic acid), citric acid, polycitric acid, anionic oligonucleotides, and multi-valent anions.

A method of the invention includes taking the nanoparticles and aggregating them into microparticles or other larger solid constructs. In a method of the invention the microparticles and other larger constructs consist of only aggregated nanoparticles. In a method of the invention the microparticles and other larger constructs consist of nanoparticles as well as additional hydrophobic materials such as a hydrophobic polymer that acts as a "glue molecule". Examples of other hydrophobic polymers that may be included include poly(lactic acid), poly(lactic-co-glycolic acid), and polycaprolactone.

In a method of the invention the microparticles are made using an emulsion process. For example, the nanoparticles may be suspended in an organic solvent (e.g., a nonpolar solvent phase) along with additional hydrophobic polymers if desired, and the suspension (inverse nanoparticle dispersion) then emulsified in an aqueous continuous phase (e.g., a polar external phase). The inverse nanoparticle dispersion can be immiscible or substantially immiscible in the polar external phase. The polar external phase can include a stabilizing polymer to prevent emulsion drops formed from coalescing. The nonpolar solvent phase can be removed to aggregate the nanoparticles to form microparticles. In this example, hardened microparticles composed of aggregated nanoparticles can be produced upon the removal of the organic solvent (nonpolar solvent phase).

In a method of the invention the microparticles are made using a spray drying process. The inverse nanoparticle dispersion can be atomized into air (or another gas), e.g., through spray drying, and the atomized inverse nanoparticle dispersion can be dried to form microparticles that can be solid and essentially dry.

In a method of the invention for encapsulating a water soluble agent, the copolymer may be a triblock copolymer comprising blocks A, B, and C. For example, the copolymer can have the form A-B-C, and each of blocks A, B, and C can be chemically distinct from the other blocks.

In a method of the invention for encapsulating a water soluble agent, the copolymer can be a triblock copolymer comprising blocks A, B, and C. The copolymer can have the form A-B-C. For example, block A can be soluble in the second polar process solvent and can be soluble in the nonprocess solvent. For example, block B can be insoluble in water and can be soluble in the nonprocess solvent. For example, block C can be insoluble in the nonprocess solvent. Block C can precipitate upon mixing of the water soluble agent solution, copolymer solution, and nonprocess solvent. Block A can be poly(ethylene glycol) (PEG), block B can be selected from the group consisting of poly(lactic acid) (PLA), poly(lactic-co-glycolic acid) (PLGA), poly(caprolactone) (PCL), and a polyester, and block C can be selected from the group consisting of poly(acrylic acid), poly(aspartic acid), and poly(glutamic acid). In an embodiment, the core can comprise block C and the shell can comprise block A and block B.

In a method of the invention for encapsulating a water soluble agent, the method can further include adding a crosslinking agent to crosslink block C. Block C can be selected from the group consisting of poly(acrylic acid), poly(aspartic acid), and poly(glutamic acid). The crosslinking agent can be a metal cation. The metal cation can be selected from the group consisting of an alkaline earth, magnesium (Mg), calcium (Ca), a transition metal, iron, and iron(III).

In a method of the invention for encapsulating a water soluble agent, the method can further include adding a crosslinking agent to crosslink block C. For example, block C can be poly(glutamic acid) and the crosslinking agent can be iron(III).

In a method of the invention for encapsulating a water soluble agent, the method can further include combining the inverse nanoparticle dispersion with a reforming solvent. Block A can be soluble in the reforming solvent, and block B can be insoluble in the reforming solvent. After the combination with the reforming solvent, the core of the inverse nanoparticle can comprise block B and block C, and the shell of the inverse nanoparticle can comprise block A. In an embodiment, block A can be poly(ethylene glycol) PEG, block B can be poly(lactic acid) (PLA), and the reforming solvent can be water.

In a method of the invention for encapsulating a water soluble agent, the copolymer can be a diblock copolymer and the water soluble agent can comprise a polysaccharide.

In a method of the invention for encapsulating a water soluble agent, the copolymer can be poly(acrylic acid)-b-poly(styrene).

In a method of the invention for encapsulating a water soluble agent, the method can further include adding a crosslinking agent to crosslink the copolymer.

In a method of the invention for encapsulating a water soluble agent, the method can further include adding a crosslinking agent to crosslink the copolymer. The copolymer can be poly(acrylic acid)-b-poly(styrene) and the crosslinking agent can be tetraethylene pentamine (TEPA).

In a method of the invention for encapsulating a water soluble agent, the first polar process solvent and the second polar process solvent can comprise tetrahydrofuran (THF), dimethyl sulfoxide (DMSO), and water. The nonprocess solvent can be chloroform and the crosslinking agent can be dissolved in the nonprocess solvent. The water soluble agent can include a polysaccharide selected from the group consisting of maltodextrin, dextran, and combinations.

In a method of the invention for encapsulating a water soluble agent, the copolymer can be poly(glutamic acid)-b-poly(lactic acid). In a method of the invention for encapsulating a water soluble agent, the copolymer can be poly (aspartic acid)-b-poly(lactic acid). The first polar process solvent can include dimethyl sulfoxide (DMSO) or dimethylformamide (DMF) and the second polar process solvent can include dimethyl sulfoxide (DMSO) or dimethylformamide (DMF). A crosslinking agent can be added to crosslink the copolymer. The crosslinking agent can be a metal cation. For example, the crosslinking agent can be iron(III).

BRIEF DESCRIPTION OF THE FIGURES

FIGS. 3A, 3B, 3C, and 3D show the particle size distribution for sets of nanoparticles formed that encapsulate various water soluble agents.

In FIGS. 8A and 8B, "Eq" represents equivalents of TEPA crosslinker with respect to acid groups on the PAA block.

DETAILED DESCRIPTION

Figure 1:
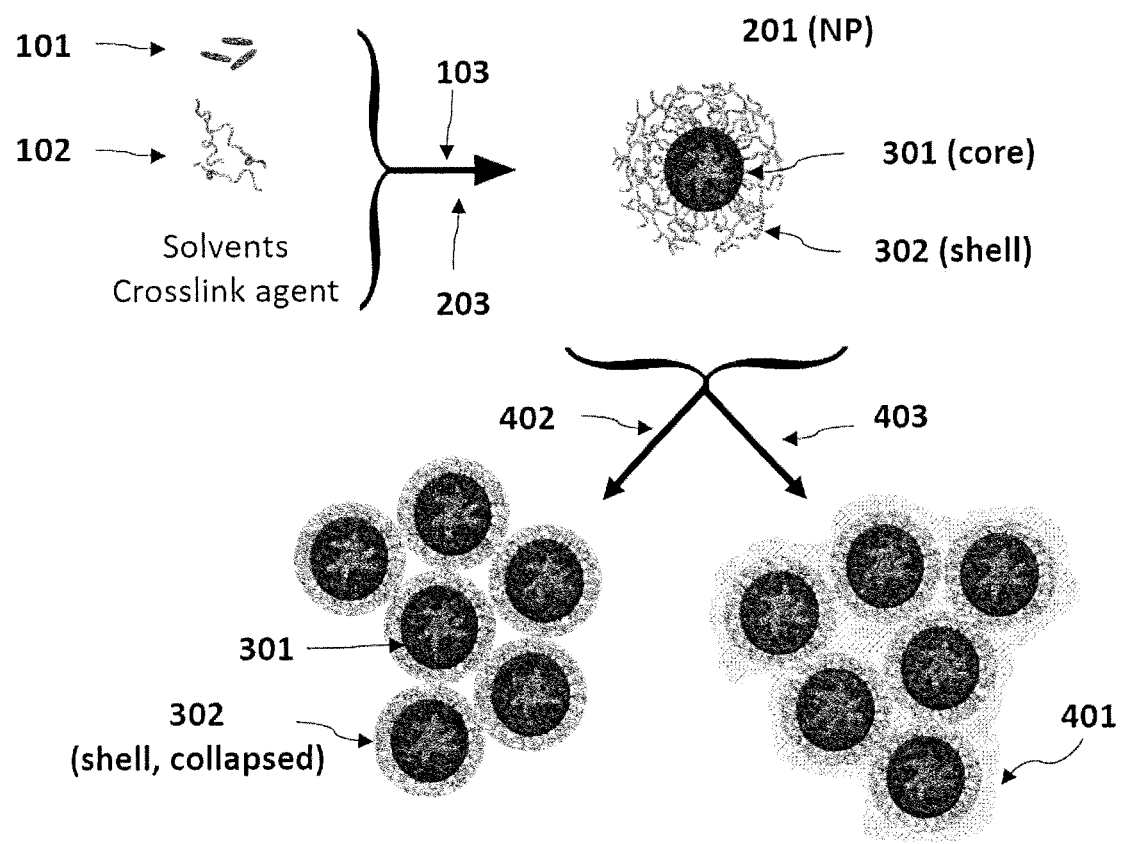
FIG. 1 illustrates steps in the production of nanoparticles and microparticles according to the invention. An "inverse" nanoparticle 201 can be formed of a copolymer 102 that assembles into a nanoparticle having a hydrophilic core 301 including a water soluble agent 101 and a less polar shell 302. The core can be crosslinked to form an "inverse" nanoparticle with a crosslinked core 203. "Inverse" nanoparticles can be aggregated into a microparticle 402. Alternatively, the "inverse" nanoparticles can be aggregated 403 into a microparticle along with an additional hydrophobic matrix 401, that, for example, can include an additional polymer that acts as a "glue molecule".

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference in their entirety as if each had been individually incorporated. For example, published international patent application nos. WO/2015/200054 (PCT/US2015/036060, Pagels et al.) and WO/2015/130835 (PCT/US2015/017590, Prud'homme et al.) are each hereby incorporated by reference in their entirety.

Encapsulation and delivery of soluble therapeutics and biologics, including peptides, proteins, DNA, and RNA, is challenging. Biologics can exhibit poor stability, fast clearance times, immune recognition, and high costs. Nanoparticles, microparticles, and larger monoliths capable of releasing soluble therapeutics in a controlled manner that will protect them from degradation, clearance, and immune recognition are desired. Biologics are presently commonly delivered via injection, thus controlled release may reduce the frequency of drug administration and increase patient compliance.

It has been possible to make nanoparticles by rapid precipitation processes, described in U.S. Pat. No. 8,137,699 B2. However, these previous examples involved hydrophobic core materials that precipitated out of an aqueous phase upon mixing. It was unexpected that the process could be completely inverted and that a water soluble compound could be precipitated into a hydrophobic solution. It was unexpected that copolymers could be used in a reverse way in which the polar component is oriented inside the core of the particle and the hydrophobic less polar component is oriented into the less polar solution phase with stable particles, i.e., "inverse" nanoparticles, resulting.

In this specification, the terms "nanoparticles", "particles", and "nanocarriers" are used interchangeably, unless a distinction is indicated by the context. Particles according to the invention that have hydrophilic or more polar cores are at times referred to as "inverse particles", to contrast them with particles that have hydrophobic or less polar cores. However, for the sake of brevity, when the context indicates that particles having hydrophilic or more polar cores according to the invention are being discussed, these may be simply referred to as "particles" or "nanoparticles".

Nanoparticles are particles with hydrodynamic mass average diameters as determined by dynamic light scattering to be between 10 nm and 800 nm, for example, between 10 nm and 800 nm. Microparticles are aggregates of the nanoparticles and can have average sizes from 1 micron to 1 or 2 mm. These larger sizes have to be determined by Mie Scattering or from microscopic images.

All solvents are miscible to some degree in each other. Miscible solvents are used in the initial nanoparticle precipitation process. "Miscible" solvents as referred to herein are those that when mixed at the ratios used in the nanoparticle formation process or the microparticle process would produce solutions that have no more than 20% of the volume of the minor phase (e.g., a polar process solvent) not dissolved in the majority phase. Completely miscible solvents as referred to herein are those that when mixed at the ratios used in the nanoparticle formation process or the microparticle process would produce solutions with no phase separation. Immiscible solvents are used in the microparticle formation process when an immiscible emulsion process is employed in microparticle formation. "Immiscible" solvents as referred to herein are those that when mixed at the volume ratios used in the microparticle formation process produce less than 20% reduction in the volume of the minor phase due to solubilization into the majority phase.

The development of injectable polymeric depots for the prolonged release of biologics is a complex engineering challenge of optimizing biologic stability, encapsulation efficiency, loading, and release profile, as well as ease and scalability of production. That is, the delivery system for a biologic should protect, prolong the release of, reduce clearance times of, and reduce the frequency of administration of the biologic, as well as target the tissue(s) of interest. The aqueous processing conditions and lack of hydrophobic interfaces in hydrogel based delivery systems make them suitable for maintaining protein stability. However, the diffusion controlled release from these systems makes it difficult to produce degradable injectable gels capable of releasing biologics over periods of months or longer. Hydrophobic scaffolds are adept at more prolonged release, but the formulation methods can be too harsh for most large proteins. In the double emulsion method for forming nanocarriers, it is difficult to increase loading, increase encapsulation efficiency, increase protein stability, or optimize the release profile without negatively affecting another parameter. It is important to understand these constraints in order to design new formulation methods. For example, newly investigated approaches of post-loading porous poly(lactic-co-glycolic acid) (PLGA) capitalize on fundamental research into the closure of pores on the microparticle surface during burst release as well as previous observations that protein desorption from the PLGA walls plays an important role in controlling the release rate. Ultimately, protein and peptide therapeutics cover a broad range of molecules, each with particular physical characteristics and processing needs; it is unlikely that a single polymeric depot will be suitable for the delivery of every biologic.

The delivery of agents such as protein and peptide therapeutics or other biologics from polymeric systems can be through release from a monolith, or release from micro or nanoparticles. Monoliths include erodible implantable devices. Micro and nanoparticles may be delivered systemically or in a local depot.

Release of therapeutics from polymeric systems may be controlled in one of two ways. In the first method, the therapeutic is conjugated to the polymeric material of the scaffold. The therapeutic is released when it is cleaved from the scaffold. This is most commonly done with hydrogels. Because conjugation entails the formation of new chemical bonds, the system is subject to more rigorous FDA approval and is thus generally undesirable. In the second method, the soluble therapeutics are encapsulated within an insoluble but erodible matrix. The erodible matrices are hydrophobic and must be processed with hydrophobic organic solvents. This method may be preferable because there is no chemical modification to the therapeutic.

Soluble materials can be encapsulated without chemical modification through either (1) mixing the material directly with a scaffold material (example: PLGA) in an organic solvent or (2) forming an emulsion. In method (1), the hydrophilic material often aggregates in the organic solvent. As the solvent is removed, even at low loadings, these aggregates produce percolating pathways resulting in an unfavorable burst release of encapsulated material. In order to improve the release profile, process (2) can be used. The soluble material is contained in an aqueous phase that is encapsulated in an outer, nonmiscible, organic solvent containing a hydrophobic scaffold material. Percolation is prevented and the emulsion is stabilized through the use of small molecule or polymeric surfactants. The emulsion process is completed in batches, which is not optimal for large scale production. Additionally, the high shear rates involved in the emulsification process may denature proteins and cleave DNA.

Processing biologics in the presence of organic solvents or under high shear conditions leads to denaturation and irreversible aggregation, which results in loss of therapeutic activity and potential immunogenicity. A number of approaches for avoiding denaturation and improving the stability of biologics during processing have been developed. One technique (U.S. Pat. No. US2012230913-A1) is the formation of tunable and reversible nanoclusters of proteins which assemble at high protein concentrations in a buffered aqueous environment in the presence of a high volume fraction (~0.3) of an "extrinsic crowder" such as trehalose. When buffered at the isoelectric point, the low electrostatic repulsions and the crowder-driven protein-protein attractions result in nanoclusters of proteins on the order of 100 nm which revert to active monomers upon dilution. The dense protein phase stabilizes the native structure and retains therapeutic activity due to the disfavoring of unfolding (Johnston et al., Concentrated dispersions of equilibrium protein nanoclusters that reversibly dissociate into active monomers. ACS Nano. (2012) 1357-1369). Other protein-dense phases (gels) have been formed from the addition of salts under controlled pH conditions and have demonstrated storage stability (Johnson & Lenhoff, Characterization and suitability of therapeutic antibody dense phases for subcutaneous delivery. Molecular Pharmaceutics. (2013) 3582-3591). Such dense phases can be used to improve stability during handling of process streams containing proteins.

Flash NanoPrecipitation (FNP) is a previously patented process (U.S. Pat. No. 8,137,699 (herein, "'699 patent"), hereby incorporated by reference in its entirety herein) to make nanoparticles with a hydrophobic core and hydrophilic stabilizing shell (Johnson, B. K., et al., AIChE Journal (2003) 49:2264-2282). This process allows for the high loading of hydrophobic material and can reproducibly produce particles ranging in size from the micelle size of the stabilizing material up to several hundred nanometers. Currently, the use of FNP has been limited to the encapsulation of core material with high log P values (hydrophobic). Flash NanoPrecipitation technology can encapsulate biologics with high encapsulation efficiency and loadings greater than 75 wt %.

In a method according to the invention, FNP is used to make nanoparticles that can function as or enhance the efficacy of vaccines or other immunomodulatory compositions. For example, these nanoparticles can include vaccines, adjuvants, and/or other agents (examples of vaccines, adjuvants, and other agents are in published international patent application WO2014/165679 (Sosin et al.) and published U.S. patent applications US2010/0233251 (von Adrian et al.) and US2011/0293701 (Bratzler et al.), each of which are hereby incorporated by reference in their entirety).

In a method according to the invention, polymer protected core shell nanoparticles are made by rapid precipitation, so that the resulting particles contain hydrophilic material in their core, and an organic-solvent soluble (less hydrophilic) shell. These nanoparticles having a hydrophilic core and a less hydrophilic shell can be termed "inverse" nanoparticles, in contrast with the nanoparticles of the '699 patent having a hydrophobic core and a hydrophilic shell.

These "inverse" particles may be processed by covalently or non-covalent stabilizing the particles, adding a second coating of stabilizing material (layer by layer FNP), and/or by incorporating them into larger monoliths or microparticles.

Nanoparticle Formation

Flash NanoPrecipitation Process

The Flash NanoPrecipitation (FNP) process can be used to create "inverse" particles with hydrophilic cores and/or with encapsulated water soluble agents, such as hydrophilic peptides. The process is illustrated in FIG. 1. A copolymer 102 can be dissolved in a polar process solvent at a concentration of at least 0.1% by weight, but preferably the concentration of copolymer is at least 0.2% by weight to form a first process solution. In an embodiment, the copolymer can be dissolved in the polar process solvent at a concentration in a range of from about 0.1 wt %, 0.2 wt %, 0.5 wt %, 1 wt %, 2 wt %, 5 wt %, 10 wt %, or 20 wt % to about 0.2 wt %, 0.5 wt %, 1 wt %, 2 wt %, 5 wt %, 10 wt %, 20 wt %, or 40 wt %. A person of skill in the art will appreciate that a factor such as the economics of a process can constrain a lower bound of concentration, and that factors such as the viscosity of the process solution or the solubility limit of the copolymer in the polar process solvent can constrain an upper bound of concentration. For example, if the viscosity of the first process solution is much greater than that of the nonprocess solvent, mixing of the first process solution with the nonprocess solvent may be inhibited. A person of skill in the art will appreciate that factors such as the molecular weight of the copolymer and the composition of the copolymer can affect the maximum concentration that can be attained in the polymer solution before the viscosity becomes too high.

Examples of copolymers include but are not limited to block copolymers, graft copolymers, and random copolymers that contain regions with different solvent solubilities within the same copolymer. For example, a poly(n-butyl acrylate)-block-poly(acrylic acid) (PBA-b-PAA) diblock copolymer can be used. Examples of process solvents include, but are not limited to, water, alcohols, acetone, acetonitrile, glycol ethers, dimethyl sulfoxide (DMSO), dimethylformamide, and mixtures thereof. The process solvent can be heated or pressurized or both to facilitate dissolution of the copolymer, depending on the dissolution characteristics of the copolymer in the solvent.

Upon micromixing 103 the process solvent containing the copolymer with a less polar non-process solvent, the dissimilar solubility characteristics of regions or portions of the copolymer are manifested and the more polar portions of the copolymer can no longer exist in the soluble state, so that an "inverse" nanoparticle 201 precipitates.

In an embodiment, additive water soluble target molecules 101, for example, a hydrophilic peptide, can be added to the copolymer 102 in the process solvent. Upon creation of nanoparticles 201 with the copolymer, the additive target molecule 101 will be incorporated in the nanoparticle. Additive target molecules 101 that are poorly soluble in the non-process solvent are coated, encapsulated, or confined as a particulate core and sterically stabilized by the protective colloid of the copolymer 102. The nanoparticles maintain a small and stable size in the nonprocess solvent.

In another embodiment (not shown in FIG. 1), the target material and copolymer are dissolved in separate process solvent streams. The process solvent used to dissolve the copolymer and the process solvent used to dissolve the target material may be, but are not required to be, the same. For example, the target material (water soluble agent) can be dissolved in a first polar process solvent to form a water soluble agent solution, and the copolymer can be dissolved in a second polar process solvent to form a copolymer solution. These streams, the water soluble agent solution and the copolymer solution, are mixed, e.g., simultaneously mixed, with the nonprocess solvent to form a mixed solution. The first polar process solvent and the second polar process solvent can be miscible, or they can be completely miscible (i.e., so that another phase is not formed) at the volumetric ratios at which they are mixed. The first polar process solvent and the nonprocess solvent can be miscible, or they can be completely miscible (i.e., so that another phase is not formed) at the volumetric ratios at which they are mixed. The second polar process solvent and the nonprocess solvent can be miscible, or they can be completely miscible (i.e., so that another phase is not formed) at the volumetric ratios at which they are mixed. Thus, the resultant mixed solution can be of a single phase or more than one phase. In another embodiment, the target material and copolymer are dissolved in a single process solvent stream. This stream is then rapidly mixed with a nonprocess solvent.

The intense micromixing 103 of the process solution and the non-process solvent can be effected in any number of geometries. The essential idea is that high velocity inlet streams cause turbulent flow and mixing that occurs in a central cavity. The time for process solvent/non-process solvent mixing is more rapid than the assembly time of the nanoparticles. While not meant to be limiting, two such geometries have been previously described and analyzed: the Confined Impinging Jet mixer (CIJ) (Johnson, B. K., Prud'homme, R. K. Chemical processing and micromixing in confined impinging jets. *AIChE Journal* 2003, 49, 2264-2282; Liu, Y., Fox, R. O. CFD predictions for chemical processing in a confined impinging-jets reactor. *AIChE Journal* 2006, 52, 731-744) and the multi-inlet vortex mixer (MIVM) (Liu, Y., Cheng, C., Liu, Y., Prud'homme, R. K., Fox, R. O. Mixing in a multi-inlet vortex mixer (MIVM) for flash nanoprecipitation. *Chemical Engineering Science* 2008, 63, 2829-2842). These examples are meant to be illustrative rather than limiting or exhaustive.

The fast mixing and high energy dissipation involved in this process provide mixing timescales that are shorter than the timescale for nucleation and growth of particles, which leads to the formation of nanoparticles with active agent loading contents and size distributions not provided by other technologies. When forming the nanoparticles via Flash NanoPrecipitation, mixing occurs fast enough to allow high supersaturation levels, for example, as high as 10,000, of all components to be reached prior to the onset of aggregation. The supersaturation level is the ratio of the actual concentration of a material, for example, a copolymer, in a solvent to the saturation concentration of that material in that solvent. For example, the supersaturation levels can be at least about 1, 3, 10, 30, 100, 300, 1000, or 3000 and can be at most about 3, 10, 30, 100, 300, 1000, 3000, 10,000, 30,000, or 100,000. The timescales of aggregation of the target material and copolymer self-assembly are balanced. Therefore, the target material and polymers precipitate simultaneously, and overcome the limitations of low active agent incorporations and aggregation found with the widely used techniques based on slow solvent exchange (e.g., dialysis). The Flash NanoPrecipitation process is essentially insensitive to the chemical specificity of the components, making it a universal nanoparticle formation technique.

Figure 2B:
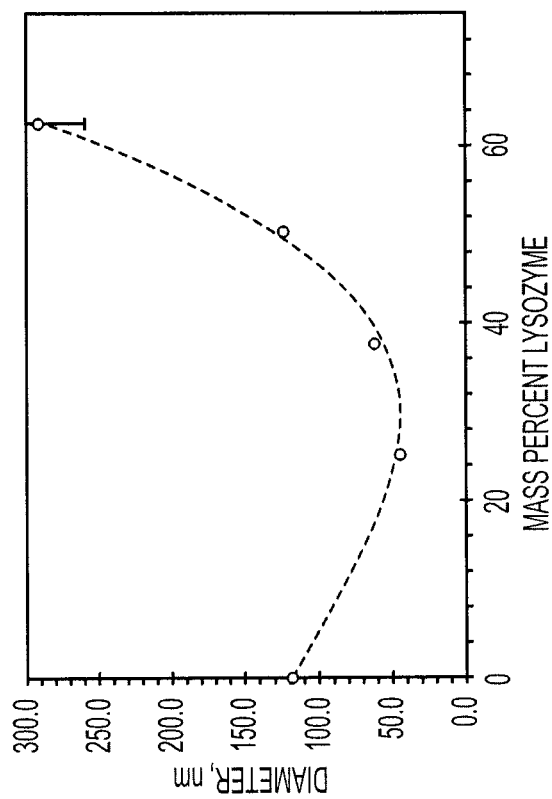
FIGS. 2A, 2B, 2C, and 2D illustrate how the variation of parameters in the Flash NanoPrecipitation process can control the diameter of the nanoparticles formed.
Figure 2A:
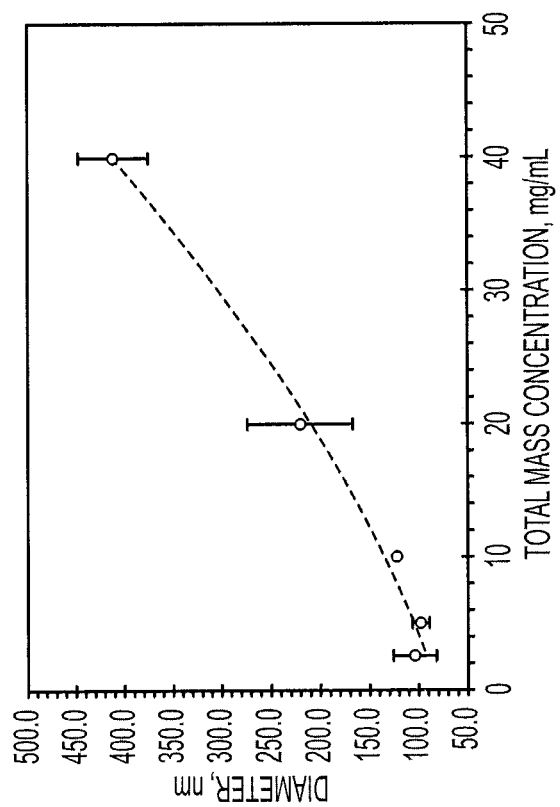
Figure 2D:
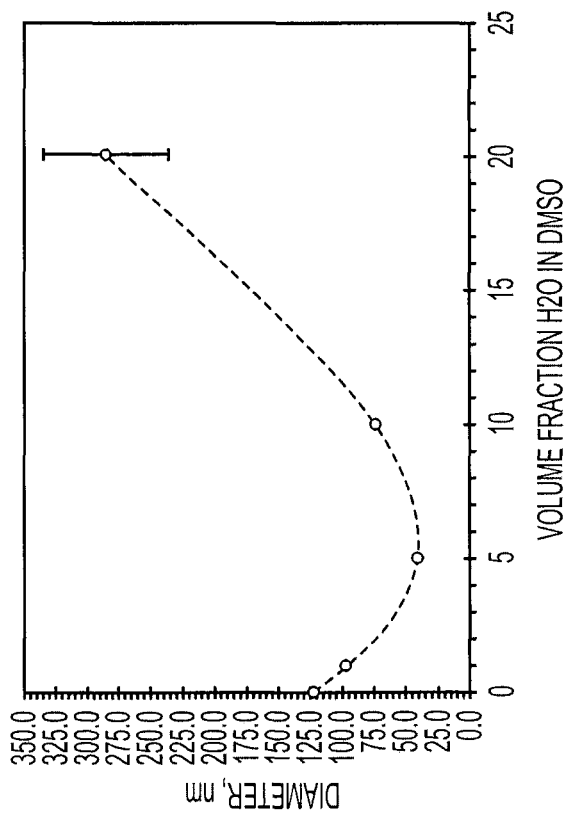
Figure 2C:
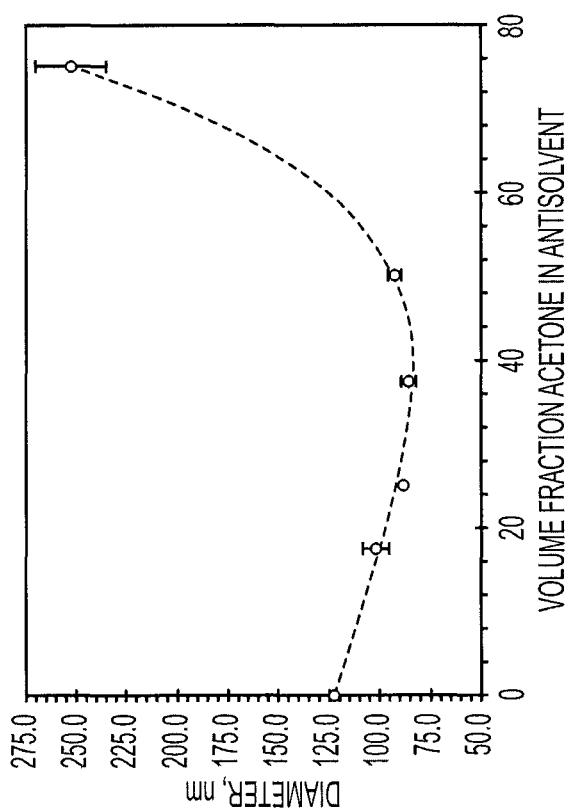

The size of the resulting nanoparticles from this process can be controlled by controlling the mixing velocity used to create them, the total mass concentration of the copolymer and target molecules in the process solvent, the process and non-process solvents, the ratio of the copolymer and target molecule, and the supersaturation of the target molecule and non-soluble portion of the copolymer upon mixing with the non-process solvent. That is, there are a number of "handles" that can be used to control the size and particle size distribution of the nanoparticles. For example, in the formation of particles including lysozyme as the target molecule, the nanoparticle diameter can be varied with the total mass concentration as shown in FIG. 2A, with the mass percent of the target molecule lysozyme (mass percent of lysozyme with respect to lysozyme plus copolymer) as shown in FIG. 2B, with the volume fraction of acetone (fraction of acetone with respect to acetone plus chloroform) in the nonprocess solvent (antisolvent), the acetone being a poorer solvent for the hydrophilic lysozyme than the chloroform, as shown in FIG. 2C, and with the volume fraction of water ($H_2O$) in dimethylsulfoxide (DMSO) in the polar process solvent as shown in FIG. 2D. The experimental conditions under which this information was obtained is shown in Table 1, below.

particles formed, i.e., with more nucleation sites more, but smaller, particles are formed. At higher acetone concentrations, as the acetone concentration is increased, the rate of aggregation of the lysozyme protein is enhanced and this dominates the size of the particles formed. As the volume fraction of water is increased (FIG. 2D), the process solvent becomes more polar. At lower water concentrations, as the water concentration is increased, the water acts as a nucleation site, helping the core of the nanoparticle to pack more tightly, so that the size of the nanoparticles decreases. At higher water concentrations, as the water concentration is increased, the water becomes integrated into the core, so that the size of the nanoparticles increases.

Nanoparticles as small as 40 nm diameter can be obtained at 50% loading (loading being the percentage of water soluble agent with respect to the water soluble agent plus copolymer). Stable nanoparticles can be obtained with 75% loading, although the diameter of the nanoparticles became too large to measure using dynamic light scattering (DLS).

Nanoparticles can be produced from copolymers that are dissolved in a process solvent with no target material added.

Using the methods according to the invention, particles can be made that have sizes in the range of 15 nm to 10500 nm, sizes in the range of 20 nm to 6000 nm, sizes in the

TABLE 1

| Agent, Effect Studied, & Fig. | Process Stream | Nonprocess Stream | Bath |
|---|---|---|---|
| Lysozyme, Effect of loading on nanoparticle (NP) size, FIG. 2B | 500 uL DMSO, lysozyme and polymer at varying ratios, (lysozyme + polymer) = 10 mg/mL | 500 uL $CHCl_3$ | 4.5 mL $CHCl_3$ |
| Lysozyme, Nonprocess solvent effect, FIG. 2C | 500 uL DMSO, 5 mg/mL lysozyme, 5 mg/mL polymer | 500 uL antisolvent mixture | 4.5 mL antisolvent mixture |
| Lysozyme, Total mass concentration, FIG. 2A | 500 uL DMSO, equal masses of lysozyme and polymer | 500 uL $CHCl_3$ | 4.5 mL $CHCl_3$ |
| Lysozyme, Water effect, FIG. 2D | 500 uL DMSO with set vol % MQ, 5 mg/mL lysozyme, 5 mg/mL polymer | 500 uL $CHCl_3$ | 4.5 mL $CHCl_3$ |

Without being bound by theory, for example, as the total mass concentration is increased (FIG. 2A), the protein aggregation rate can grow more quickly than the nucleation rate of polymer self-assembly. At lower mass percentages of lysozyme, as the mass percentage of lysozyme is increased (FIG. 2B), the size initially decreases. Without being bound by theory, this may be because of a faster nucleation rate, i.e., with more nucleation sites there are more, but smaller, particles. Alternatively, this may be because of better packing of the PAA blocks, i.e., the negative charges of the PAA repel, and water and/or other core materials can shield this effect. At higher mass percentages of lysozyme, as the mass percentage of lysozyme is increased, the size increases. Without being bound by theory, this may be because at high percentages, large particles form because they have a higher volume to surface area ratio than small particles. As the volume fraction of acetone in the nonprocess solvent (antisolvent) is increased (FIG. 2C), the nonprocess solvent becomes less polar. At lower acetone concentrations, as the acetone concentration is increased, the diameter of the particles formed decreases, because the nucleation rate of the copolymer increases and this dominates the size of the range of 20 nm to 1000 nm, sizes in the range of 35 nm to 400 nm, or sizes in the range of 40 nm to 300 nm. Sizes can be determined by dynamic light scattering. For example, particles can be made that have sizes of at least about 15 nm, 20 nm, 35 nm, 40 nm, 50 nm, 100 nm, 200 nm, 300 nm, 400 nm, 600 nm, 900 nm, 1000 nm, 2000 nm, 4000 nm, or 6000 nm, and have sizes of at most about 20 nm, 35 nm, 40 nm, 50 nm, 100 nm, 200 nm, 300 nm, 400 nm, 600 nm, 900 nm, 1000 nm, 2000 nm, 4000 nm, 6000 nm, or 10500 nm. Sizes reported and cited herein are the intensity average reported values as determined by the Malvern Nanosizer deconvolution program for particles smaller than 2000 nm, and determined by scanning electron micrcoscopy, or optical microscopy and image analysis using Image J for sizes greater than 2000 nm. Other intensity weighted deconvolution methods can be used to determine sizes of the nanoparticles.

Encapsulated Material

Encapsulated material (target molecules) must be sufficiently polar that it rapidly precipitates in the less polar non-process solvent. Molecules that do not meet these criteria may be chemically modified to increase their water solubility and propensity to precipitate in the organic nonprocess solvent. Examples of biologic material that may be encapsulated include, but are not limited to, peptides, proteins, DNA, RNA, saccharides, and derivatives, conjugates, and/or analogs thereof. For example, glucagon-like peptide-1 (GLP-1) may be encapsulated. Small molecule water soluble therapeutics and imaging agents may also be encapsulated. Soluble stabilizing agents may be encapsulated in particles to provide stability to the particle for its use or for subsequent processing steps. Any of these materials may also be co-precipitated within a single particle. Hydrophilic material may be encapsulated for the sole purpose of adding stability to the particles during post processing. For example, material with molecular weights between 100 and 10,000,000 Daltons (Da) may be encapsulated. Material with molecular weights between 250 and 10,000,000 Da may be encapsulated. Material with molecular weights between 100 and 1,000,000 Da may be encapsulated. Material with molecular weights between 250 and 1,000,000 Da may be encapsulated. Material with molecular weights between 100 and 200,000 Da may be encapsulated.

Certain encapsulated materials may be multifunctional. For example, tobramycin is cationic and can itself be crosslinked with a copolymer. Other cationic active materials, with multiple cationic residues will similarly crosslink the anionic polymer blocks.

The encapsulated material may be incorporated into the particle at a range of loadings. For example, the mass of the encapsulated material may be greater than or equal to the mass of the copolymer. For example, the concentration of the encapsulated material in the first process solution may be from about 0.1 wt %, 0.2 wt %, 0.5 wt %, 1 wt %, 2 wt %, 5 wt %, 10 wt %, or 20 wt % to about 0.2 wt %, 0.5 wt %, 1 wt %, 2 wt %, 5 wt %, 10 wt %, 20 wt %, or 40 wt %.

In order to encapsulate target molecules that are susceptible to denaturation due to shear stress or organic solvents, including but not limited to peptides and proteins, they may be stabilized. One can achieve this through the generation of protein dense phases such as nanoclusters in the process solvent prior to continuous mixing with the non-process solvent. These nanoclusters may then be incorporated into nanoparticles using an FNP process. The nanocluster characteristics are determined by selection of solvent, buffer type and concentration, extrinsic crowder type and concentration, and protein concentration. Johnston et al. provided suitable conditions for the formation of nanoclusters in (U.S. Pat. No. US2012230913-A1). A person of skill in the art will appreciate that optimal parameters will be dictated by the physical properties of the protein target molecule such that attraction and repulsion forces are balanced and physical or chemical stability is not negatively affected. For example, the process solvent may be a high dielectric constant polar solvent such as water or dimethylsulfoxide, provided it does not result in protein denaturation. For the polar solvent, a buffer may be selected so that the system is at or near the isoelectric point of the target molecule. A person of skill in the art will appreciate that parameter selection will also be guided by design considerations such as target nanoparticle size and costs. For example, protein and extrinsic crowder concentrations dictate nanocluster size, which controls nanoparticle generated by Flash NanoPrecipitation. Johnston et al. provided suitable protein and extrinsic crowder concentration ranges and protein to extrinsic crowder ratios for nanocluster formation in (U.S. Pat. No. US2012230913-A1). The desired process solvent composition may be obtained through resuspension of lyophilized protein or via centrifugal filtration of a stream more dilute than the target composition.

Johnston et al. have given a list of suitable extrinsic crowders such as a glycerol, an erythritol, an arabinose, a xylose, a ribose, an inositol, a fructose, a galactose, a maltose, a glucose, a mannose, a trehalose, a sucrose, a polyethylene glycol, an amino acid, peptide, a carbomer 1342, a glucose polymers, a silicone polymer, a polydimethylsiloxane, a polyethylene glycol, a carboxy methyl cellulose, a poly(glycolic acid), a poly(lactic-co-glycolic acid), a polylactic acid, a dextran, a poloxamers, organic co-solvents selected from ethanol, N-methyl-2-pyrrolidone (NMP), PEG 300, PEG 400, PEG 200, PEG 3350, propylene glycol, N,N-dimethylacetamide, dimethylsulfoxide, solketal, tetrahydrofurfuryl alcohol, diglyme, ethyl lactate, a salt, a buffer or a combination thereof (U.S. Pat. No. US2012230913-A1). The extrinsic crowder may alternatively solely be the copolymer which will assemble to form the core and shell of the nanoparticle after mixing with the non-process solvent or this copolymer may be added in combination with one or more additional extrinsic crowders. One can select the extrinsic crowder, so that it is soluble in both the process solvent and the non-process solvent. One can alternatively select an extrinsic crowder that is insoluble in the non-process solvent and will precipitate into the nanoparticle core which is forming around the protein nanoclusters and provide stability to the protein. One can dissolve extrinsic crowder in the non-process solvent such that overall crowder concentration is not changed during continuous mixing of streams in FNP.

The mass ratio of copolymer to target molecule can be adjusted. This may be for the purpose of modulating extrinsic crowder effects or for nanoparticle stability and size control. Copolymer solubility limitations can dictate a number of different processing configurations using the CIJ and MIVM in order to obtain the desired initial and final copolymer concentrations. One can dissolve the copolymer completely in the nanocluster process stream. One can dissolve the copolymer completely in a process stream separate from the nanocluster process stream. These process streams may be the same polar solvent or may be different solvents. They may be equal volume or may be different. If one generates nanoclusters at very high protein concentrations, one can use a smaller volume of this process stream compared to the copolymer process stream to obtain the desired mass ratio and final composition. One may dissolve the copolymer in part in the nanocluster process stream and in part in a separate process stream as described above.

In one embodiment, the target molecule is aggregated in a dense phase prior to introduction of the non-process solvent. In this embodiment, the target molecule is in aggregated in a dense phase in the process solvent and not molecularly dissolved. Whereas the timescales of nucleation, growth, and copolymer assembly were critical when the target molecule is molecularly dissolved, in this instance the system must be designed such that the time scale of nanocluster dissociation is longer than assembly of the copolymer on the surface of these nanoclusters, forming and stabilizing the nanoparticles. For example, to provide greater nanocluster persistence, one can reversibly crosslink proteins using commercially available ester or disulfide linkages. In doing this, one can also provide an additional lever to manipulate controlled release profiles.

In another embodiment, the protein dense phase is not formed from nanoclusters assembled due to crowding effects but from the addition of an appropriate precipitant such as sodium citrate.

Examples of suitable polar process solvents include, but are not limited to, water, alcohols, methanol, ethanol, dimethyl formamide (DMF), dimethyl sulfoxide (DMSO), acetonitrile, acetone, N-methyl pyrrolidone (NMP), and mixtures thereof. The process solvent (or solvents) is chosen so that the copolymer is molecularly dissolved, as defined in the following section. The process solvent containing the protein nanoclusters must allow for their stable formation and not result in denaturation of the biologic.

Suitable non-process solvents include, but are not limited to, chloroform, dichloromethane, alkanes such as hexane, ethers such as diethyl ether, tetrahydrofuran (THF), toluene, acetone, and mixtures thereof. The nonprocess solvent is chosen such that the copolymer rapidly precipitates on the protein nanoclusters to form stable nanoparticles.

The characteristics of suitable copolymers are listed in a subsequent subsection. The nanoparticles may be cross-linked by a variety of methods as described in a subsequent section.

Solvents

Formation of nanoparticles requires one or more process solvents and a non-process solvent stream. The process and non-process solvents may be a pure (that is, a single) liquid compound or a mixture of two or more pure liquid compounds. Other non-liquid compounds that aid in the solvent quality of the streams may be added and are also considered part of the solvent. For example, a surfactant, a salt, or a cosolvent may be added to a solvent and considered part of the solvent. These excipient compounds may or may not be in the final nanoparticle or microparticle construct, depending on the requirements of the final product.

The polar process solvent containing the copolymer is chosen such that the copolymer is molecularly dissolved. This requires that the process solvent solubilize all parts of the copolymer. The process solvent containing the material to be encapsulated, if present, is also chosen such that material is molecularly dissolved. In some cases, if nanoclusters are formed prior to nanoparticle assembly, the process solvent containing the nanoclusters is chosen such that the clusters are stable and suspended. In this embodiment of the invention, the material to be encapsulated will not be molecularly dissolved in the process solvent. These process solvents may be, but are not required to be, the same. In some cases, both the copolymer and material to be encapsulated may be dissolved in a single solution of the process solvent. In order to dissolve the water soluble material to be encapsulated, the process solvent is more polar than the non-process solvent. Examples of process solvents include, but are not limited to, water, alcohols, methanol, ethanol, glycol ethers, dimethyl formamide (DMF), dimethyl sulfoxide (DMSO), acetonitrile, acetone, N-methyl pyrrolidone (NMP), and mixtures thereof. Acids, bases, and salts are a few examples of additives that may be used to aid in the solubilization of the copolymer and encapsulated material in the process solvent. The process solvent can be buffered to the isoelectric point of the biologic when generating protein nanoclusters. Extrinsic crowders listed previously may also be included in the process solvent in order to form and maintain the stability of nanoclusters.

The solutions of process solvent containing copolymer and material to be encapsulated are mixed with a nonprocess solvent. The non-process solvent must be capable of changing the local molecular environment of the copolymer and causing local precipitation of the more polar sections of the polymer. The nonprocess solvent is chosen such that the more polar sections of the copolymer rapidly precipitate and the more nonpolar (less polar) sections of the copolymer remain solubilized. Thus, the copolymer will self-assemble into micelles or other structures in the nonprocess solvent. The nonprocess solvent is chosen such that the target material to be encapsulated rapidly precipitates in the final mixture. In the case of process streams containing preformed protein nanoclusters, the nonprocess solvent is chosen such that the nanoclusters persist and the copolymer assembles with the nanoclusters localized to the core of nanoparticles. In most cases it is preferable for the process and non-process solvents to be fully miscible at the final composition. In some cases, no more than 20 volume percent of the process solvent may phase separate in the final composition. In general, this is only acceptable if the phase separated solvent goes to the core of the particles and there is no macroscopic separation. Nonprocess solvents include, but are not limited to, chloroform, dichloromethane, alkanes such as hexane, ethers such as diethyl ether, tetrahydrofuran (THF), toluene, acetone, and mixtures thereof. Acids, bases, and salts are a few examples of additives that may be used to aid in the precipitation of the encapsulated material and sections of the copolymer. Solvent choices are made based on the solubilities of the copolymer and encapsulated materials. It is important to note that process solvents of one system may work well as the nonprocess solvent in another system, thus the examples given above for process and nonprocess solvents should not be considered distinct. Extrinsic crowders listed previously may be dissolved in the nonprocess solvent to maintain nanocluster stability during FNP.

Copolymers

The stabilizing polymer can be a copolymer of a more polar block coupled with a more nonpolar (less polar) block. The term "block" may be interpreted as either a distinct domain with a single molecular composition, or it may mean a region of the polymer chain which has regions that are predominantly more polar and other regions that are less polar. The polarity may be imparted by the monomers comprising the polymer backbone or grafted pendant groups or chains attached to the main polymer backbone. For example, the copolymer may be amphiphilic (the more nonpolar block is not water soluble), however, this is not a requirement and copolymers may be fully water soluble or fully non-water soluble, as long as solubilities of the blocks differ significantly enough in the nonprocess solvent. The copolymer should self-assemble in the nonprocess solvent, with the more polar blocks precipitating and the more nonpolar blocks remaining soluble. When used in the FNP process to make particles, the more polar blocks go to the core of the particle, and the more nonpolar blocks form a sterically protective shell. The sterically protective shell prevents particle aggregation and prevents percolation of encapsulated material during post processing steps.

Nanoparticles formed by the disclosed process can be formed with graft, block, or random copolymers. For example, these copolymers can have a molecular weight between about 1000 g/mole and about 1,000,000 g/mole, or between about 3000 g/mole and about 25,000 g/mole, or at least about 2000 g/mole.

The copolymers are comprised of repeat units or blocks that have different solubility characteristics. Typically, these repeat units are in groups of at least two comprising a block of a given character. Depending on the method of synthesis, these blocks could be of all the same repeat unit or contain different repeat units dispersed throughout the block, but still yielding blocks of the copolymer with polar and more non-polar portions. These blocks can be arranged into a series of two blocks (diblock) or three block (triblock), or more (multiblock), forming the backbone of a block copolymer. In addition, the polymer chain can have chemical moieties covalently attached or grafted to the backbone. Such polymers are graft polymers. Block units making up the copolymer can occur in regular intervals or they can occur randomly making a random copolymer. In addition, grafted side chains can occur at regular intervals along the polymer backbone or randomly making a randomly grafted copolymer. In graft polymers, polar blocks may be grafted on a non-polar polymer. More commonly, non-polar blocks are grafted on a more polar polymer chain. In graft copolymers, the length of a grafted moiety can vary. Preferably, the grafted segments are equivalent to 2 to 22 ethylene units in length. The grafted hydrophobic groups which create at least one less polar region of the copolymer may comprise tocopherol, tocopherol derivatives, lipids, alcohols with carbon numbers from 12 to 40, cholesterols, unsaturated and/or hydrogenated fatty acids, salts, esters or amides thereof, fatty acids mono-, di- or triglycerides, waxes, ceramides, cholesterol derivatives, or combinations. In addition, the grafting of the polymer backbone can be useful to enhance solvation or nanoparticle stabilization properties.

The copolymer used in the compositions and methods of the invention may be comprised of blocks of at least two repeat units or with a minimum contour length the equivalent of at least 25 ethylene units. Contour lengths are the linear sum of the polymer backbone, the molecular dimensions of which can be approximated using the Polymer Handbook, 4th Edition, eds. J. Brandrup, E. H. Immergut, and E. A. Grulke, assoc. ed. A. Abe, D. R. Bloch, 1999, New York, John Wiley & Sons, which is hereby incorporated by reference in its entirety.

Examples of suitable nonpolar blocks in a copolymer include but are not limited to the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, vinyl phenols and vinyllimidazole; aminoalkyls including aminoalkylacrylates, aminoalkylsmethacrylates, and aminoalkyl(meth)acrylamides; styrenes; cellulose acetate phthalate, cellulose acetate succinate, hydroxypropylmethylcellulose phthalate, poly(D,L-lactide), poly (D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), lactic acid, caprolactone, glycolic acid, and their copolymers (see generally, Illum, L., Davids, S. S. (eds.) Polymers in Controlled Drug Delivery Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., it al., Advanced Drug Delivery Reviews (2002) 54:169-190), poly(ethylene-vinyl acetate) ("EVA") copolymers, silicone rubber, polyethylene, polypropylene, polydienes (polybutadiene, polyisoprene and hydrogenated forms of these polymers), maleic anhydride copolymers of vinyl methylether and other vinyl ethers, polyamides (nylon 6,6), polyurethane, poly(ester urethanes), poly(ether urethanes), poly(esterurea). For example, polymeric blocks can include poly(ethylenevinyl acetate), poly(D,L-lactic acid) oligomers and polymers, poly(L-lactic acid) oligomers and polymers, poly(glycolic acid), copolymers of lactic acid and glycolic acid, poly(caprolactone), poly(valerolactone), polyanhydrides, copolymers of poly(caprolactone) or poly(lactic acid), or poly(propylene sulfide). For non-biologically related applications polymeric blocks can include, for example, polystyrene, polyacrylates, and butadienes.

Natural products with sufficient hydrophobicity to act as the non-polar portion of the polymer include: hydrophobic vitamins (for example vitamin E, vitamin K, and vitamin A), carotenoids, and retinols (for example, beta carotene, astaxanthin, trans and cis retinal, retinoic acid, folic acid, dihydrofolate, retinylacetate, retinyl palmintate), cholecalciferol, calcitriol, hydroxycholecalciferol, ergocalciferol, alpha-tocopherol, alpha-tocopherol acetate, alphatocopherol nicotinate, estradiol, lipids, alcohols with carbon numbers from 12 to 40, cholesterols, unsaturated and/or hydrogenated fatty acids, salts, esters or amides thereof, fatty acids mono-, di- or triglycerids, waxes, ceramides, cholesterol derivatives or mixtures thereof. For example, a natural product is vitamin E which can be readily obtained as a vitamin E succinate, which facilitates functionalization to amines and hydroxyls on the active species.

Examples of suitable polar blocks in an amphiphilic polymer that is a block copolymer include, but are not limited to the following: carboxylic acids including acrylic acid, methacrylic acid, itaconic acid, and maleic acid; polyoxyethylenes or polyethylene oxide; polyacrylamides and copolymers thereof with dimethyl-aminoethyl-methacrylate, diallyl-dimethyl-ammonium chloride, vinylbenzyl trimethylammonium chloride, acrylic acid, methacrylic acid, 2-acryamideo-2-methylpropane sulfonic acid and styrene sulfonate, polyvinyl pyrrolidone, starches and starch derivatives, dextran and dextran derivatives; polypeptides, such as polylysines, polyarginines, polyaspartic acids, polyglutamic acids; poly hyaluronic acids, alginic acids, polylactides, polyethyleneimines, polyionenes, polyacrylic acids, and polyiminocarboxylates, gelatin, and unsaturated ethylenic mono or dicarboxylic acids. To prepare anionic copolymers, acrylic acid, methacrylic acid, and/or poly aspartic acid polymers can be used. To produce cationic copolymers, DMAEMA (dimethyl aminoethyl methacrylate), polyvinyl pyridine (PVP), and/or dimethyl aminoethyl acrylamide (DMAMAM) can be used. A listing of suitable polar, water soluble, polymers can be found in Handbook of Water-Soluble Gums and Resins, R. Davidson, McGraw-Hill (1980).

The lists above of nonpolar and polar polymers should not be considered exclusive of one another. Copolymers of two polymers given in a single list may have sufficient differences in solubilities in a given nonprocess solvent to be used in this process. As an illustrative example, poly(ethylene oxide) and poly(acrylic acid) are both given in the list of polar polymers. However, poly(ethylene oxide) is soluble in chloroform and acetone, while poly(acrylic acid) is not. Therefore, copolymers of poly(ethylene oxide) and poly (acrylic acid) may be used in this process with chloroform or acetone as the nonprocess solvent.

For example, a polyanhydride and/or a polyester may be used to form a polar block and/or a nonpolar block of a block copolymer. Such a polyanhydride and/or polyester can be biodegradable and can be based on amino acids (i.e., the polyanhydride and/or polyester can be formed of amino acid monomers, as well as other monomers). The amino acids can be naturally occurring proteinogenic amino acids, naturally occurring nonproteinogenic amino acids, and/or artificially synthesized amino acids or combinations. The amino acids can be D- and/or L-amino acids. For example, the amino acids can be modified to include an additional carboxylic acid group. That is, the amino acids that serve as monomers can be dicarboxylic acids, for example, formed by coupling an amino acid to another molecule having a carboxylic acid group or by coupling an amino acid to another amino acid through the amino group. For example, the amino acids that serve as monomers can include one or a combination of the following structures:

OC—R—NR'—Z—R"—COO;

OC—R—NR'—Z—R"—Z—NR'—COO;

OC—R—NR'—X—NR'—R—COO;

OC—R—NR'—Z—R"—R—COO—R'"—O;

OC—R—NR'—Z—R"—Z'NR'—COO—R'"—O;

OC—R—NR'—X—NR'—R—COO—R'"—O, with R being an aliphatic, aromatic, or heterocyclic amino acid residue, with R' being H, alkyl (for example, having from 1 to 10 carbons) or a direct bond, with R" and R'" being the same or different aliphatic, aromatic, or heterocyclic residue(s), with Z being C=O (e.g., forming an amide moiety), COO (e.g., forming a urethane moiety), (C=O)—R"—(C=O) (e.g., an imide or forming an imide), CO—NR' (e.g., forming a urea), or =N (e.g., forming an azo, with X being an azo (N=N), urea (NR'—CO—NR'), or thiourea (NR'—CS—NR'). The polyanhydride or polyester segment can have different substituents in different portions, for example, a segment formed of OC—R—NR'—Z—R"—COO units can have Z be C=O for one or more units and have Z be COO for one or more other units. Some polyanhydrides and polyesters are described in U.S. Pat. No. 4,999,417 (A. Domb), which is hereby incorporated by reference in its entirety.

Nanoparticle Processing
Particle Stabilization

The particles are formed and stable in the organic nonprocess solvent. In most applications, it is required that the final construct be stable in aqueous environments for a set, nonnegligible amount of time. In order to process the particles into an aqueous environment, particle stabilization is required. Without stabilization, the particle may dissolve, aggregate, and/or release the water soluble target material from the core.

In an embodiment according to the invention, sections of the core of the particle may be stabilized The core refers to the more polar sections of the copolymer and encapsulated material. Material may be incorporated into the core specifically for the purpose of particle stabilization. For example, the portions of the copolymer in the core may be crosslinked 203 to form a particle with a crosslinked core 301. In another embodiment, the shell 302 of the particle may be stabilized. The shell refers to the more nonpolar sections of the copolymer that are soluble in the nonprocess solvent.

Stabilization can involve the formation of new covalent bonds. For example, the copolymer of the core (and, in some cases, the encapsulated material) of the particle may be cross-linked through the formation of new covalent bonds. The bonds may be formed directly between groups on the copolymer. Covalent bonds may be formed by adding a crosslinking material to the core for the specific purpose of cross-linking the polymer in the core. The crosslinking material (stabilizing material) may be added to the core of the particle during the FNP process. For example, the crosslinking material can be included in the process solvent.

As another example, the crosslinking material can be included in the nonprocess solvent.

Alternatively, the crosslinking material may be added to the solution after the particle has formed. For example, the particle may be "incubated" with a crosslinking material, such as a metal salt, and the crosslinking material may interact with a more polar portion of the copolymer, e.g., PAA, for example, through ionic and/or chelation effects. The degree of crosslinking realized can then be characterized by suspending the particle in a good solvent for the more polar portion of the copolymer. Particles with tight (dense) crosslinking can exhibit minimal swelling and can be associated with high levels of metal partitioning into the hydrophilic core and strong metal interactions with the more polar part of the polymer. Particles with loose crosslinking can exhibit high levels of swelling and can be associated with low levels of metal partitioning into the hydrophilic core and weak metal interactions with the more polar part of the polymer. If the partitioning of the metal into the core is very low and or the interaction of the metal with the more polar part of the polymer is very weak, then the particle may disassemble and dissolve in the solvent.

If the crosslinking material is added after the particles have been formed, the crosslinking may be diffusion limited and only occur on the outer layers of the core. If the crosslinking material is added to the solution after the particles have been formed, the particle may be cross-linked throughout the core if the core is swollen with solvent or if the cross-linking material is small enough to diffuse throughout the core. The shell of the particle may be cross-linked through the formation of new covalent bonds. The bonds may be formed directly between groups on the copolymer, or through the addition of an extra crosslinking material.

Examples of covalent chemistries that may be used include, but are not limited to carbodiimide coupling of carboxylic acids to alcohols or carboxylic acids to amines, the coupling of activated esters to alcohols or amines, maleimide-thiol chemistry, Michael addition, azidealkyne "click" chemistry, UV or light activated chemistries, and/or disulfide formation.

Stabilization can be obtained through non-covalent interactions. The core of the particle may be cross-linked through non-covalent interactions. The interactions may be directly between groups on the copolymer. Non-covalent interactions may be formed by adding a crosslinking material to the core for the specific purpose of cross-linking the polymer in the core. This crosslinking material may be added to the core of the particle during the FNP process. Alternatively, this crosslinking material may be added to the solution after the particle has formed. If the crosslinking material is added after the particles have been formed, the crosslinking may be diffusion limited and only occur on the outer layers of the core. If the crosslinking material is added to the solution after the particles have been formed, the particle may be crosslinked throughout the core if the core is swollen with solvent or if the crosslinking material is small enough to diffuse throughout the core. The shell of the particle may be cross-linked through noncovalent interactions. The interactions may be formed directly between groups on the copolymer, or through the addition of an extra crosslinking material.

Examples of non-covalent interactions that may be used include, but are not limited to, ionic interactions, acid-base interactions, metal chelation, interactions between polyhistidines and a metal such as nickel, and/or strong hydrogen bonding. An example of non-covalent particle stabilization is the use of Cr(III) to stabilize the poly(acrylic acid) core of a nanoparticle. For example, chromium (III) acetate and/or chromium (III) bromide can be used as crosslinking materials. The crosslinking may proceed through ligand exchange. The solvents used can act as ligands. For example, the interaction of the cation in a crosslinking salt should be stronger with the more polar portion of the copolymer to be crosslinked in the core than with the anion in the salt.

Other crosslinking materials (crosslinking agents) that can be used to induce non-covalent crosslinking include alkaline earth halides, magnesium halides, calcium halides, metal halides, transition metal halides, and iron halides. Metal salts can be used. Additional crosslinking materials that can be used are metal acetates, alkaline earth acetates, transition metal acetates, and calcium acetate. The crosslinking ability of a given cation (e.g., a metal) depends on the accompanying anion. The crosslinking ability of a crosslinking material, e.g., a salt, can depend on the process solvent and nonprocess solvent used. A crosslinking material can include a metal that is biological interesting or functional or otherwise useful. For example, Fe(III), Ca(II), and Zn(II) cations are biocompatible. Gd(III) (gadolinium(III)) is active in magnetic resonance imaging (MRI), and, therefore, can be useful as a tracer.

Some crosslinking materials that work well when conducting crosslinking during nanoparticle formation, e.g., during the FNP process, include polyamines, such as spermine, and certain chloride salts, such as magnesium chloride, calcium chloride, and iron(III) chloride. For example, such crosslinking materials can be used with PBA-b-PAA copolymer, methanol, dimethylsulfoxide, and/or water as the process solvent, and acetone and/or chloroform as the nonprocess solvent. It may be necessary to include some water in the process solvent for the crosslinking to occur. In some systems, calcium chloride, magnesium chloride, and spermine may act as weak crosslinkers. An iron(III) salt, such as iron(III) chloride, may induce strong crosslinking.

Multiple types of stabilization chemistries may be employed within a given particle. Stabilization may occur in the core, in the shell, at the interface, or in multiple locations within a given particle.

For many applications, particle degradation and release of encapsulated material is required. The type of stabilization chemistry used, and the density of the crosslinked network, may affect the degradation kinetics of the particle. The type of stabilization chemistry used, and the density of the cross-linked network, may also or alternatively affect the release kinetics of encapsulated material from the core of the particle.

For some applications, it is required that the encapsulated material is not chemically modified. In these cases, non-covalent interactions should be used to stabilize the particle. However, covalent crosslinking may be used as long as the chemistry is specific to the copolymer and does not modify the encapsulated material.

Particle Incorporation into Microparticles and Monoliths

The particles may be incorporated into microparticles (e.g., as 402 or 403 in FIG. 1) or larger monoliths. The hydrophobic polymer block prevents percolation and allows for high loading of the encapsulated material, stabilization during processing, and controlled release. The hydrophobic block of the amphiphilic polymer provides a uniform barrier layer thickness around each hydrophilic-core nanoparticle. Therefore, release is controlled by the more uniform hydrophobic block layer. Hydrophilic blocks of various molecular weights can be incorporated into the nanoparticle formation process to effect different release profiles. The hydrophobic block condenses around the more polar core of the primary nanoparticles that are aggregated to form the microparticle. This hydrophobic "shell" provides the primary control of release. The shell has the thickness determined by the molecular weight and concentration of the hydrophobic amphiphilic portions of the stabilizing polymer. For block copolymers the molecular weight of the hydrophobic block can be greater than or equal to 1000, 2000, 4000, 5000, 7500, or 10,000 Daltons (Da). For example, the molecular weight of the hydrophobic block can be less than or equal to 2000, 4000, 5000, 7500, 10,000, 30,000, 100,000, 300,000, or 1,000,000 Da. Supplemental hydrophobic, biocompatible polymers or hydrophobic compounds can be added during the aggregation step to further tune the release kinetics.

This shell provided by the condensed non-polar, hydrophobic amphiphilic polymer component is an important distinction between this disclosed process and previous sustained microparticle constructs. In previous approaches it is the continuous matrix phase that provides the barrier that controls release. The thickness of this matrix, which surrounds the hydrophilic actives in older technology, varies in thickness by virtue of the finite size of the hydrophilic inclusion relative to the size of the microparticle. This is described in the article J. Controlled Release 219 519-535 (2015).

If the particles are being incorporated into a hydrophobic scaffold that is processed in a poor solvent for the particle core, the particle is stabilized by the less polar polymer block prior to the aggregation step.

The hydrophilic active compound or biologic compound is captured in the interior of the particle formed by the first processing step into the hydrophobic process solvent. Organic polymers (e.g., hydrophobic polymers) soluble in the hydrophobic process solvent may be added to the particle dispersion. Polymers that might be added include biocompatible and or biodegradable polymers. Nonlimiting examples of these polymers would include: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate and copolymers of these acrylates; acrylonitriles; methacrylonitrile; vinyls including vinyl acetate, vinyl versatate, vinyl propionate, vinyl formamide, vinyl acetamide, vinyl pyridines, vinyl phenols and vinyl imidazole; amino alkyls including amino alkyl acrylates, amino alkyl methacrylates, and aminoalkyl(meth)acrylamides; styrenes; cellulose acetate phthalate, cellulose acetate succinate, hydroxypropylmethylcellulose phthalate, poly(D,L lactide), poly (D,L-lactide-co-glycolide), poly(glycolide), poly(hydroxybutyrate), poly (alkylcarbonate) and poly(orthoesters), polyesters, poly (hydroxyvaleric acid), polydioxanone, poly(ethylene terephthalate), poly(malic acid), poly(tartronic acid), poly-anhydrides, polyphosphazenes, poly(amino acids) and their copolymers, polycaprolactones, polypropylene sulfides (see generally, Illum, L., Davids, S. S. (eds.) Polymers in Controlled Drug Delivery Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., et al., Advanced Drug Delivery Reviews (2002) 54:169-190), poly (ethylene-vinyl acetate) ("EVA") copolymers, silicone rubber, polyethylene, polypropylene, polydienes (polybutadiene, polyisoprene and hydrogenated forms of these polymers), maleic anyhydride copolymers of vinyl methylether and other vinyl ethers, polyamides (nylon 6,6), polyurethane, poly(ester urethanes), poly(ether urethanes), poly(esterurea). Examples of polymeric blocks include poly(ethylenevinyl acetate), poly (D,L-lactic acid) oligomers and polymers, poly(L-lactic acid) oligomers and polymers, poly (glycolic acid), copolymers of lactic acid and glycolic acid, poly(caprolactone), poly(valerolactone), polyanhydrides, copolymers of poly(caprolactone) or poly(lactic acid). For example, polystyrene, polyacrylates, and butadienes can be used as polymeric blocks for non-biologically related (as well as for biologically related) applications. Such a hydrophobic polymer can act as a glue molecule that binds inverse nanoparticles into a microparticle. For example, the glue molecule can be chemically the same as (or chemically different than) the less polar region of the copolymer that forms the shell of a nanoparticle. For example, the glue molecule can have the same or a similar molecular weight as (or a greater molecular weight or a lesser molecular weight than) the less polar region of the copolymer. The glue molecule may act to modify the release (from the microparticle) rate of the water soluble agent.

For example, a polyanhydride and/or a polyester and/or a polyanhydride-polyester copolymer and/or a copolymer including a polyanhydride and/or a polyester segment soluble in the hydrophobic process solvent can be added to the particle dispersion. Such a polyanhydride and/or polyester can be biodegradable and can be based on amino acids (i.e., the polyanhydride and/or polyester can be formed of amino acid monomers, as well as other monomers), as described above.

Hydrophobic compounds can also be added to the nonpolar solvent phase prior to the aggregation step to assist in microparticle or matrix formation or to aid in control of the release of the active. For biological applications, biocompatible compounds may be desired. These include, but are not limited to tocopherol, tocopherol derivatives, lipids, alcohols with carbon numbers from 12 to 40, cholesterols, unsaturated and/or hydrogenated fatty acids, salts, esters or amides thereof, fatty acids mono-, di- or triglycerides, waxes, ceramides, cholesterol derivatives or mixtures thereof. Such hydrophobic, biocompatible compounds can migrate to the surface of the inverse nanoparticles or the microparticle to form a biocompatible layer. For non-biologic applications hydrophobic compounds that are soluble in the nonpolar solvent phase can be used without regard to biocompatibility.

After addition of these polymers or mixtures thereof, the resulting dispersed biologic particles in the polymer-containing hydrophobic organic solution phase can be forming into the desired microparticle or monolith by techniques well known in the field. These include emulsion-stripping techniques as described by Domb (U.S. Pat. No. 5,578,325) or Gibson (U.S. Pat. No. 6,291,013 B1), spray drying, or molding to form a solid matrix containing the encapsulated hydrophilic active, such as a biologic. The matrix can be dried by spray drying, by pan drying, or by molding processes to obtain a solid final matrix containing the encapsulated active or biologic. Dried matrix phases can be ground or micronized to make microparticles in the size range of 1 micron to 1 to 2 mm. Release is then effected by dissolution, erosion, or swelling of the matrix phase. This encapsulation followed by matrix formation enables much higher loadings of the hydrophilic active or biologic than can be achieved by simple double emulsion techniques which have been described previously in the literature. The older double emulsion routes suffer from burst release at high loadings of the active in the matrix formulation. The current process enables high loadings of active. Loadings of 1 wt %, 5 wt %, 10 wt %, 25 wt %, 45 wt %, 50 wt %, 65 wt %, 75 wt % and 85 wt % are most desirable. Burst release is limited to less than 25% release in the first 20 minutes. Also, the encapsulation efficiency of the process is uniquely high. Encapsulation efficiency, defined as the percent of the original active charged to the process relative to the active in the final microparticle, can be greater than 75%, 85%, 90% or 95%.

EXAMPLES

Example 1: Particle Assembly and Morphology

To produce particles containing hydrophilic compounds, poly(n-butyl acrylate) 7.5 kDa-b-poly(acrylic acid) 5.5 kDa (PBA-b-PAA) and the biologic were first dissolved in a polar organic solvent such as DMSO or methanol. In an FNP process, this stream was rapidly mixed with a less polar nonprocess solvent such as chloroform ($CHCl_3$) or acetone in a CIJ mixer. The non-solvent caused the biologic to precipitate. This precipitation was halted by the self-assembly of the hydrophilic PAA block of the PAA-b-PBA on the growing particle surface. The final particles were sterically stabilized in the non-solvent by the hydrophobic PBA block. The resultant nanoparticle had a core-shell structure.

This process has been applied to an assortment of model hydrophilic agents with varying molecular weights, including lysozyme as a model protein (14.3 kDa), the cyclic peptide antibiotic vancomycin (1.45 kDa), a model 7-amino acid long peptide (glycine-arginine-leucine-glycine-tryptophan-serine-phenylalanine (GRLGWSF), 822 Da), the dyes eosin Y (692 Da) and tartrazine (534 Da), the MRI contrast agent gadopentetic acid (548 Da), the aminoglycoside antibiotic tobramycin (468 Da), glutathione (307 Da), and tryptophan (204 Da). Each formulation resulted in nanoparticles with low polydispersities at a minimum loading of 50 wt %.

Example 2: Nanoparticle Loading and Size Control

The sizes of particles produced with FNP may be controlled through the time scales for precipitation of the core material, as well as through the time scale for polymer self-assembly. These time scales are modulated through material concentrations as well as through the choice of nonprocess solvent.

Increasing the percentage of core material necessitated the formation of larger particles. For both lysozyme and vancomycin, the particle size initially decreased as biologic was added compared to the micelle size of the block copolymer. This may be because the addition of core material allows the PAA to more tightly pack due to charge shielding effects. Very high loadings of both lysozyme and vancomycin were obtained. Loading of lysozyme as high as 75 wt % was obtained without the formation of large precipitates, however, the particles were too large to analyze using dynamic light scattering (DLS). Vancomycin loadings up to 90 wt % resulted in stable particles, with sub-100 nm particles observed for loadings below 80 wt %. These loadings indicated that, despite its high water solubility and poor solubility in chloroform, vancomycin played a role in stabilizing the surface—most likely through its aromatic groups.

Additional process variables that were found to impact the particle size included the total mass concentration of polymer and biologic in the DMSO stream, the volume fraction of acetone in the chloroform stream, and the volume fraction of water in the DMSO stream. The addition of 5 vol % water in the DMSO stream reduced the size of the 50% loaded lysozyme particles from 125 nm to 45 nm. With the proper formulation parameters, nanoparticles with loadings greater than 50 wt % and diameters less than 100 nm were readily accessible with the FNP process. By choosing a nonprocess solvent in which the biologic is negligibly soluble the particles may have a very high (>90%) encapsulation efficiency.

Example 3: Stabilization of Nanoparticles for Further Processing

In order to stabilize the nanoparticles in aqueous environments and reduce the loss of encapsulated material during processing steps, methods of crosslinking the PAA shell in order to form a gel were investigated. Ionic crosslinking was focused on because it reduces the risk of covalently modifying the encapsulated agent. The anionic PAA side groups may be crosslinked either with multivalent metal cations or polyamines (S. Bontha, A. V. Kabanov, T. K. Bronich, Polymer micelles with cross-linked ionic cores for delivery of anticancer drugs, J. Controlled Release. 114 (2006) 163-174; T. K. Bronich, A. V. Kabanov, V. A. Kabanov, K. Yu, A. Eisenberg, Soluble Complexes from Poly(ethylene oxide)-block-polymethacrylate Anions and N-Alkylpyridinium Cations, Macromolecules. 30 (1997) 3519-3525; T. K. Bronich, P. A. Keifer, L. S. Shlyakhtenko, A. V. Kabanov, Polymer Micelle with Cross-Linked Ionic Core, J. Am. Chem. Soc. 127 (2005) 8236-8237; R. T. Patil, T. J. Speaker, Retention of trypsin activity in spermine alginate microcapsules, J. Microencapsul. 14 (1997) 469-474). The nanoparticles were successfully stabilized by including chloride salts of $Ca^{2+}$, $Zn^{2+}$, or $Fe^{3+}$ in the nonprocess solvent stream. Spermine, which contains two primary and two secondary amines, and the positively charged antibiotic tobramycin also stabilized the particles. Ionic gelation agents can be added to the nanoparticle solution after the FNP process.

Iron III chloride, included at a 3:1 ratio of acid groups to iron, was an especially effective crosslinking agent. Particles loaded with 50 wt % vancomycin and crosslinked with iron swelled minimally from 72 nm in $CHCl_3$ to 79 nm in methanol, which dissolves non-crosslinked nanoparticles. The minimum swelling indicated a small mesh size, which is necessary to slow the release of encapsulated biologics. For example, the minimal swelling in methanol indicated tight crosslinking. The iron provided enough electron contrast to allow for TEM imaging of the nanoparticles. A TEM micrograph of 20-40 nm particle cores supported the DLS data, which gave larger sizes because the measurement included the PBA shell.

Example 4: Nanoparticles Formed with Various Encapsulated Materials

Nanoparticles (NPs) with encapsulated hydrophilic model active pharmaceutical agents (APIs) were created using Flash NanoPrecipitation (FNP) using a confined impingement jets mixer (CIJ) which has been described previously. Generally, the stabilizing polymer (PBA-b-PAA) and API were dissolved in a more polar organic solvent, typically consisting of MeOH or DMSO. This stream was rapidly mixed with an equal volume stream of a more nonpolar antisolvent at equal flowrates, typically consisting of $CHCl_3$ or acetone. The outlet stream of the CIJ was collected in a stirring bath of antisolvent such that the final nanoparticle solution is 90 vol % antisolvent.

For crosslinked NPs, the crosslinking agent was included in the antisolvent stream such that the charge ratio (ratio of acid groups on the PAA to positive charge of crosslinking agent) was 1:1.

Nanoparticles with a hydrophilic core ("inverse" nanoparticles) were formed that encapsulated the small molecules tartrazine, eosin Y, and gadolinium-diethylene triamine pentaacetic acid (Gd-DTPA). The particle size distribution for the sets of particles formed with these encapsulated materials is shown in FIG. 3A.

Nanoparticles with a hydrophilic core were formed that encapsulated the biologic antibiotics tobramycin and vancomycin. The particle size distribution for the sets of particles formed with these encapsulated materials is shown in FIG. 3B.

Figure 3D:
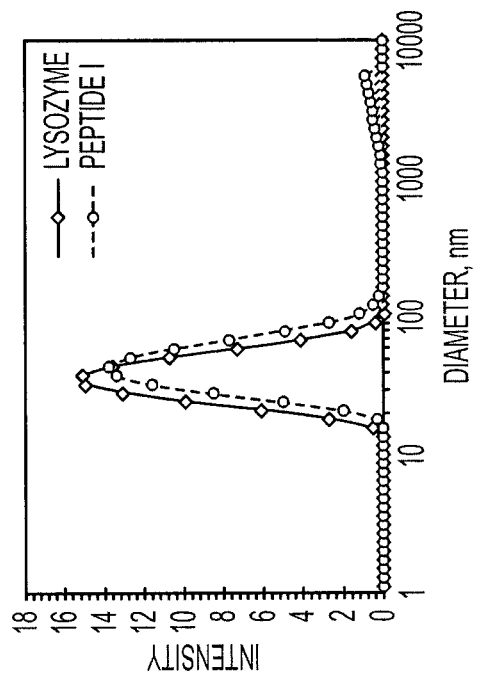
Figure 3C:
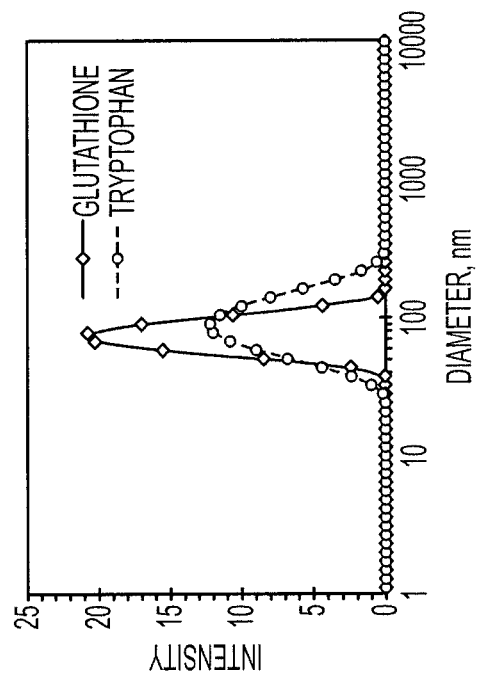
Figure 4:
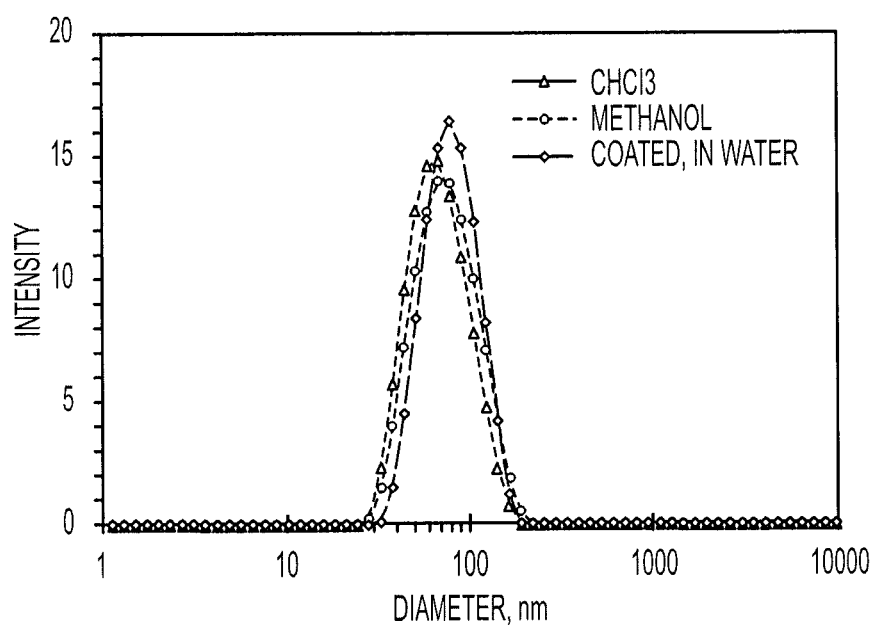
FIG. 4 shows particle size distributions for uncoated particles in chloroform ($CHCl_3$), uncoated particles in methanol (MeOH), and coated particles in water.

Nanoparticles with a hydrophilic core were formed that encapsulated the small molecule biologics glutathione and tryptophan. The particle size distribution for the sets of particles formed with these encapsulated materials is shown in FIG. 3C.

Nanoparticles with a hydrophilic core were formed that encapsulated the larger biologics lysozyme and "Peptide I" (glycine-arginine-leucine-glycine-tryptophan-serine-phenylalanine (GRLGWSF)). The particle size distribution for the sets of particles formed with these encapsulated materials is shown in FIG. 3D.

The experimental conditions used for the above-described encapsulation systems are provided in Table 2, below.

TABLE 2

| Sample | Process Stream | Nonprocess Stream | Bath |
|---|---|---|---|
| Lysozyme | 500 uL DMSO, 5 mg/mL lysozyme, 5 mg/mL polymer | 500 uL $CHCl_3$ | 4.5 mL $CHCl_3$ |
| Vancomycin | 500 uL DMSO with 5 vol % MQ 5 mg/mL lysozyme 5 mg/mL polymer | 500 uL $CHCl_3$ | 4.5 mL $CHCl_3$ |
| Pep I | 500 uL DMSO with 5 vol % MQ 5 mg/mL pepl 5 mg/mL polymer | 500 uL $CHCl_3$ | 4.5 mL $CHCl_3$ |
| Eosin Y* | 500 uL DMSO, 5 mg/mL Eosin Y, 10 mg/mL polymer | 500 uL $CHCl_3$ | 4.5 mL $CHCl_3$ |
| Tartrazine* | 500 uL DMSO with 5 vol % MQ, 5 mg/mL tartrazine, 10 mg/mL polymer | 500 uL $CHCl_3$ | 4.5 mL $CHCl_3$ |
| Gd-DTPA** | 500 uL DMSO with 5 vol % MQ, 5 mg/mL Gd-DTPA, 5 mg/mL polymer | 500 uL $CHCl_3$ | 4.5 mL $CHCl_3$ |

TABLE 2-continued

| Sample | Process Stream | Nonprocess Stream | Bath |
| --- | --- | --- | --- |
| Tobramycin | 500 uL DMSO, 10 mg/mL polymer | 500 uL DMSO, 5.5 mg/mL tobramycin (1:1 charge ratio) | 4.5 mL acetone |
| Glutathione | 500 uL DMSO with 5 vol % MQ 5 mg/mL glutathione 5 mg/mL polymer | 500 uL CHCl$_3$ | 500 uL CHCl$_3$ |
| Tryptophan**** | 500 uL DMSO with 5 vol % MQ and 5 vol % acetic acid, 5 mg/mL tryptophan, 5 mg/mL polymer | 500 uL CHCl$_3$ | 4.5 mL CHCl$_3$ |

*PBA(3 kDa)-b-PAA(12 kDa) used in these formulations, all others used PBA(7.5 kDa)-b-PAA(5.5 kDa)
**API is first dissolved in MQ (Milli-Q purified water) then diluted with DMSO
****API is first dissolved in acetic acid, then diluted with DMSO Among these encapsulated materials, the smallest encapsulated molecule had a molecular weight of 186 Da, and the largest encapsulated molecular had a molecular weight nearly two orders of magnitude greater, 14 kDa, demonstrating the versatility of this process. The encapsulated particles also had a range of charges, for example, tartrazine is negatively charged, whereas tobramycin is positively charged.

A person of skill in the art would appreciate that systems for encapsulating materials can be optimized to determine the best polar process solvent (e.g., DMSO vs. MeOH, optionally with additives), nonprocess solvent (antisolvent) (e.g., acetone, CHCl$_3$, toluene, or DCM), polymer/core material ratios, and/or water content of the solvent stream.

Example 5: PAA-b-PBA Nanoparticles

Poly(acrylic acid)-b-poly(n-butyl acrylate) (12 kDa-b-3 kDa) was dissolved in methanol at a concentration of 20 mg/mL. Basic chromium acetate was dissolved in methanol at a mass concentration of 90 mg/mL. The solutions were mixed one part polymer solution to one part chromium solution by volume. Immediately after the mixture was prepared, it was mixed 1:1 against a chloroform stream in a handheld confined impingement jet (CIJ) mixer. The effluent of the CIJ mixer was collected in a rapidly stirring bath of chloroform such that the final solvent composition was 1 part methanol to 9 parts chloroform by volume. The particles were mixed for 4 days to allow the chromium cations to crosslink the poly(acrylic acid). The resulting particles were 135 nm in chloroform with a polydispersity index (PDI) less than 0.1. Swollen in methanol, the resulting particles were 190 nm with a PDI less than 0.1. Particle diameter was measured by dynamic light scattering using a Malvern Zetasizer in normal analysis mode.

Example 6: PAA-b-PBA Nanoparticles with Glutathione

Poly(acrylic acid)-b-poly(n-butyl acrylate) (12 kDa-b-3 kDa) was dissolved in methanol at a concentration of 40 mg/mL. Reduced glutathione (GSH) was dissolved in a 1:4 mixture (volume to volume) water and methanol at a mass concentration of 20 mg/mL. Basic chromium acetate was dissolved in methanol at a mass concentration of 90 mg/mL. The solutions were mixed one part polymer solution to one part chromium solution to two parts glutathione solution by volume. Immediately after the mixture was prepared, it was mixed 1:1 against a chloroform stream in a handheld confined impingement jet (CIJ) mixer. The effluent of the CIJ mixer was collected in a rapidly stirring bath of chloroform such that the final solvent composition was 1 part water to 9 parts methanol to 90 parts chloroform by volume. The particles were mixed for 4 days to allow the chromium cations to crosslink the poly(acrylic acid). The resulting particles were 110 nm in chloroform with a PDI less than 0.1. Swollen in methanol, the resulting particles were 130 nm with a PDI less than 0.1. Particle diameter was measured by dynamic light scattering using a Malvern Zetasizer in normal analysis mode.

Example 7: PAA-b-PEG Nanoparticles with Glutathione

Poly(acrylic acid)-b-poly(ethylene glycol) (5 kDa-b-5 kDa) was dissolved in methanol at a concentration of 40 mg/mL. Reduced glutathione was dissolved in a 1:4 mixture (volume to volume) water and methanol at a mass concentration of 20 mg/mL. Basic chromium acetate was dissolved in methanol at a mass concentration of 56 mg/mL. The solutions were mixed one part polymer solution to one part chromium solution to two parts glutathione solution by volume. Immediately after the mixture was prepared, it was mixed 1:1 against a chloroform stream in a handheld confined impingement jet (CIJ) mixer. The effluent of the CIJ mixer was collected in a rapidly stirring bath of chloroform such that the final solvent composition was 1 part water to 9 parts methanol to 90 parts chloroform by volume. The particles were mixed for 4 days to allow the chromium cations to crosslink the poly(acrylic acid). The particles were diluted with acetone and centrifuged out of solution at 15000 rcf for 15 minutes. The supernatant was decanted and the pellet was resuspended in acetone. The particles were centrifuged out of solution a second time at 15000 ref for 15 minutes. The supernatant was decanted and the pellet was resuspended in deionized water. The resulting particles were 245 nm in diameter with a PDI of 0.35 or lower, as measured by dynamic light scattering using a Malvern Zetasizer in normal analysis mode.

Example 8: PAA-b-PBA Nanoparticles with Propidium Iodide

PAA-b-PBA (7.5 kDa-b-5.5 kDa) and propidium iodide (PI) were dissolved in MeOH containing 5 vol % water at a concentration of 10 mg/mL polymer and 0.1 mg/mL PI. This stream (500 μL) was rapidly mixed in a CIJ mixer with a stream consisting of 600 μL of chloroform and 50 μL of FeCl$_3$ in dissolved in MeOH such that the final ratio of Fe$^{3+}$ to PAA monomer was 1:3. This stream ejected from the CIJ mixer was collected in 4.5 mL of chloroform. The resulting ~100 nm particles were stable in chloroform and methanol, indicating that the iron had crosslinked the PAA core. The PI was determined to be bound to the PAA based on the shift in its absorbance.

Example 9: Incorporation of PAA-b-PBA Nanoparticles with Propidium Iodide into PLGA Microparticles The nanoparticles in Example 8, above, were concentrated to ~10 mg/mL by rotary evaporation. The concentrated particles we precipitated in a 20-fold volume excess of room temperature hexanes and removed from solution by centrifugation. The particles were resuspended in DCM to a concentration of 15 mg/mL along with 5 mg/mL of PLGA and 0.14 mg/mL EtTP5 (1 wt % with respect to the total hydrophobic polymer content, which is the PLGA+PBA). 50 uL of the DCM phase was added to 3 mL of a MQ solution containing 1 wt % PVA and 40 mM sodium dodecyl sulfate (SDS) which had been adjusted to a pH of 2 using HCl. The vial was gently mixed by hand to form the emulsion, and the DCM was removed by rotovap at 40° C. at 340 torr for 5 minutes followed by 200 torr for 10 minutes and 80 torr for 45 minutes.

Figure 5:
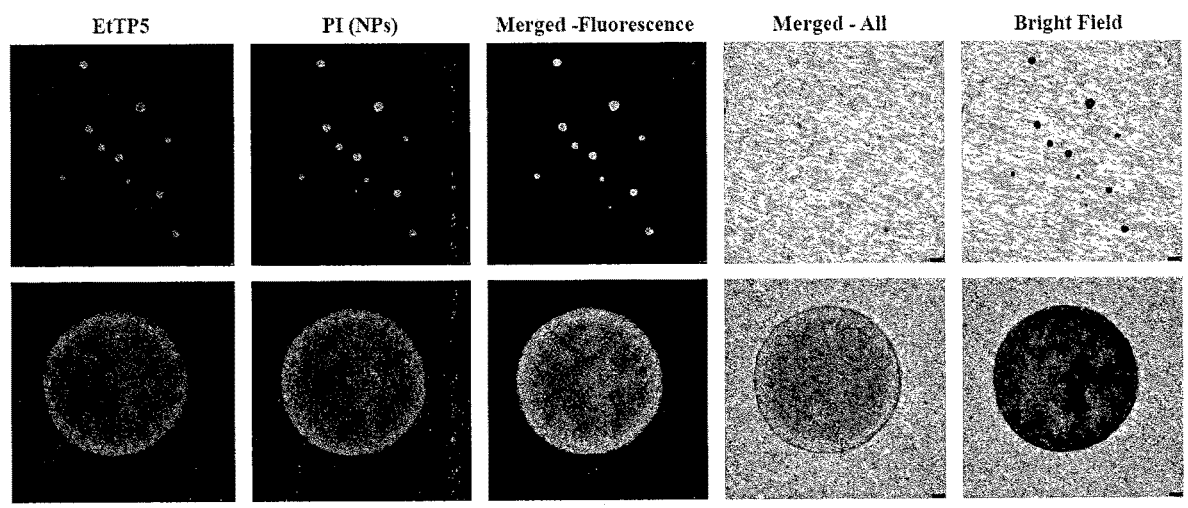
FIG. 5 shows Fluorescent images of PLGA MPs (microparticles) containing 75 wt % NPs (nanoparticles). The EtTP5 (2,2,10,10-tetraethyl-6,14-bis(triisopropylsilylethynyl)-1,3,9,11-tetraoxa-dicyclopenta[b,m]pentacene (EtTP-5)) (red) is a hydrophobic dye co-localized with the PBA and PLGA. The propidium iodide (PI) is bound to the PAA core of the NPs and shows that the NPs are distributed throughout the MPs. The top row is wide-field view taken with a 10× lens (scalebar: 100 μm). The bottom row is close-up of a single 80 μm particle taken with a 40× lens (scalebar: 7.5 μm).
Figure 6:
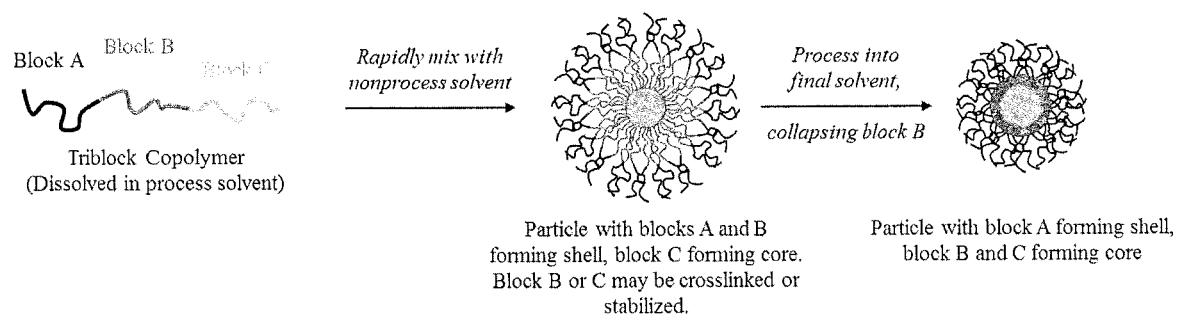
FIG. 6 shows the formation of an inverse nanoparticle dispersion with a triblock copolymer.

Following MP synthesis, the particles were imaged with a Lieca TCS SP5 Confocal microscope. Particles were imaged with a large pinhole while focused on the midplane (epifluorescence mode) using dry 10× and 40× lenses. The EtTP5 was excited a 633 nm solid state line and emission collected from 660-780 nm. The PI was excited with a 543 nm solid state line and the emission was collected from 560-660 nm. The two dyes were excited and imaged separately and these images merged into a merged image. These images are given in FIG. 5.

Example 10: Formation of an Inverse Nanoparticle Dispersion with a Triblock Copolymer An inverse nanoparticle can be formed with a triblock copolymer. The triblock copolymer can consist of three chemically distinct blocks in the order A-B-C. Block A can be soluble in water as well as in less polar organic solvents. For example, block A can be soluble in water as well as the nonprocess solvent. For example, block A can be poly(ethylene glycol) (PEG). Block B can be insoluble in water and soluble in the nonprocess solvent. For example, block B can be poly(lactic acid) (PLA), poly(lactic-co-glycolic acid) (PLGA), or poly(caprolactone) (PCL). Block C can be insoluble in the nonprocess solvent and can precipitate when the process solvent and nonprocess solvents are mixed. For example, block C can be poly(acrylic acid), poly(glutamic acid), or poly(aspartic acid).

The triblock copolymer can be dissolved in a process solvent. A water soluble material to be encapsulated can also be dissolved in the process solvent. This process solvent stream can be rapidly mixed with the nonprocess solvent, for example, using the Flash Nanoprecipitation (FNP) technique. In this solvent mixture, the water soluble material for encapsulation will precipitate. In this mixed solution mixture, block C of the triblock copolymer will precipitate, however blocks A and B remain soluble. Block C and the water soluble encapsulated material form the core of the particle, and blocks A and B form a shell in the mixed solution.

Blocks B or C can be stabilized. For example, if block C is a poly(aspartic acid), poly(acrylic acid), or poly(glutamic acid), metal cations may be used to stabilize the core. For example, Fe(III) cations may be used to crosslink poly(glutamic acid).

After nanoparticle formation, the nanoparticles may be processed into another solvent, a reforming solvent. In this reforming solvent, block A is soluble, however, block B is insoluble. Block C may be soluble or insoluble in the reforming solvent. For example, if block B is PLA and block A is PEG, the reforming solvent may be water. In the reforming solvent, block A forms a solvated shell around the particle, and blocks B and C form the core.

Example 11: Inverse Nanoparticles as Vaccines

The Flash Nanoprecipitation (FNP) process can be used to produce particles, such as inverse nanoparticles and microparticles, useful as immunomodulatory compositions, such as vaccines, glycoconjugate vaccines, and desensitizing agents for allergy treatment. For example, such immunomodulatory compositions can be used in preventing or treating infectious disease, including disease induced by fungi, bacteria, viruses, worms, and other single- and multicellular pathological agents, cancer, allergies, such as allergic asthma, autoimmunie disease, such as rheumatoid arthritis, immune suppression, for example, to prevent transplant rejection, immunization against addictive substances, and immunization against toxins.

Vaccines and allergy desensitization particles can be made by the double coating process to produce nanoparticles less than 400 nm in size, or they can be aggregated to make injectable depot formulations.

Vaccine constructs formed with FNP can be assembled in a single step without covalent modification of any of the vaccine components. Many different glycans can be introduced into the nanoparticle core to give wide spectrum immune stimulation. A protein, such as a bacterial protein toxin, can be incorporated into the nanoparticle core. For example, full CRM197 proteins (a non-toxic mutant of diphtheria toxin, useful as a carrier protein for making polysaccharides and haptens immunogenic) can be incorporated stoichiometrically into the nanoparticle cores during the rapid precipitation step of FNP, and the need for covalent reactions, which can be complex and difficult to control, can be avoided. Thus, FNP offers a flexible route for forming and ensuring the composition of multivalent vaccines. The encapsulated proteins can be in a denatured or in a native state. The vaccine nanoparticle and its contents can be processed by macrophages and other immune system cells.

Inverse nanoparticles can be used to encapsulate (load) materials that stimulate an immune response, such as an antigen, and can present such materials to cells of the immune system. For example, such cells can include B cells and/or T cells. The nanoparticles can include an immunomodulatory agent, an immunostimulatory agent, and/or a targeting agent. For example, an immunomodulatory agent can induce an immune response, or can be a polynucleotide that encodes a protein that when expressed induces and immune response. The immunomodulatory agent can be an antigen. An immunostimulatory agent can stimulate the immune system by, for example, stimulating regulatory T cells. A targeting agent can recognize a target associated with a type of cell, tissue, organ, or subcellular structure. There is a vast range of antigens or allergens, including components of foods, chemicals, drugs, e.g., antibiotics, dander, animal and plant proteins, animal venom, spores, and pollen.

The activity of a vaccine can be enhanced through an adjuvant. Adjuvants may function by trapping and providing a slow release of antigens, or may function as irritants that amplifies the immune response of a patient's body. An adjuvant may be an inorganic material, such as alum or aluminum hydroxide, or an organic material, such as mineral oil. An adjuvant may be a synthetic material or a naturally occurring compound, such as squalene, a bacterial toxin, e.g., tetanospasmin or a derivative, or an oligodeoxynucleotide (CpG ODN). An adjuvant may be hydrophilic, hydrophobic, or amphiphilic.

For example, the inverse nanoparticle functioning as an immunomodulatory composition may include an immunomodulatory agent, immunostimulatory agent, or targeting agent such as a protein, carbohydrate, glycoside, glycoprotein, nucleic acid, nucleoprotein, lipid, glycolipid, lipopolysaccharide, a toll-like receptor agonist (e.g., vesicular *stomatis* virus glycoprotein (VSV-G), a bacterial lipopolysaccharide, or a high-mobility group protein (such as HMGB-1)), dead, inactivated, or attenuated organisms (such as bacteria) or viruses, portions of an organism (such as a bacterium) or virus, such as a protein coat. For example, the immunomodulatory agent may be hydrophilic and incorporated inside the core of the inverse nanoparticle. As another example, the immunomodulatory agent may be amphiphilic and incorporated partially inside the core and partially inside the shell of the inverse nanoparticle. Or, the immunomodulatory agent may be hydrophobic and incorporated inside the shell of the inverse nanoparticle. An inverse nanoparticle may incorporate more than one type of immunomodulatory agent. For example, it can be useful to incorporate a hydrophobic targeting agent in the shell of the inverse nanoparticle, and sequester a hydrophilic immunomodulatory or immunostimulatory agent, such as a hydrophilic protein, within the core of the core of the inverse nanoparticle for delayed release. The incorporation of sequestering of an agent may be the result of noncovalent interactions, for example, hydrogen bonding or electrostatic interactions.

The inverse nanoparticle may incorporate materials or compounds, so that it has dual or multifunctionality. For example, the inverse nanoparticle may include both an immunomodulatory agent, such as a polysaccharide, to stimulate an immune response to bacterium or class of bacteria and an antibiotic drug, such as ciprofloxacin, for example, for the prevention and/or treatment of typhoid. For example, the inverse nanoparticle may include both an immunomodulatory agent, such as a viral protein, and an antiviral medication, such as lamivudine, for example, for the prevention and/or treatment of hepatitis B.

The inverse nanoparticle functioning as an immunomodulatory composition or vaccine may include a biocompatible or biodegradable polymer, such as polycaprolactone or a polymer formed of monomeric units that are natural occurring or derived from naturally occurring compounds, for example, poly(lactic acid), poly(glycolic acid), or a poly (amino acid), such as poly(glutamic acid) and poly(aspartic acid). Copolymers of such biodegradable polymers, e.g., poly(lactic-co-glycolic acid) (PLGA), and copolymers of a biodegradable polymer and a nonbiodegradable polymer can be used.

The shell of the inverse nanoparticle can be crosslinked to enhance stability and control release of an agent incorporated into the shell or into the core.

For example, a pneumococcal vaccine, such as a conjugated vaccine having the immunogenic diphtheria toxoid CRM197 covalently bound to capsular polysaccharides that stimulate the immune response to *Streptococcus pneumoniae*, can be added to a polar process solvent, such as water, along with the triblock copolymer of Example 10, to form a water soluble vaccine-triblock copolymer solution. For example, the triblock copolymer can be PEG (block A)-b-PLGA (block B)-b-poly(aspartic acid) (block C). The non-process solvent can have a hydrophobic (or less hydrophilic) adjuvant, such as squalene, added to it to form a nonprocess solution. The water soluble vaccine-triblock copolymer solution can then be rapidly mixed with the nonprocess solution through the Flash Nanoprecipitation (FNP) technique. The inverse nanoparticles formed can sequester the conjugated vaccine in the hydrophilic core formed by the block C (poly(aspartic acid)) segments, and can sequester the squalene adjuvant in the less hydrophilic shell formed by the block B-block A (PLGA-b-poly(aspartic acid)) segments.

Example 12: Release Assay with Poly(Acrylic Acid)-b-Poly(Styrene) Inverse Nanoparticles Encapsulating Polysaccharides Maltodextrins (MD) with average molecular weights of 1000 g/mol ("1 k") and 3275 g/mol ("3 k") as well as a dextran (Dex) at 20,000 g/mol ("20 k") were conjugated with 7-Amino-4-methylcoumarin (AMC) via a reductive amination mediated by sodium cyanoborohydride. Nuclear Magnetic Resonance (NMR) was used to confirm the structure and the conjugation extent. The polysaccharides were dissolved with poly(acrylic acid)$_{4.8k}$-b-poly(styrene)$_{5k}$ (PAA-b-PS) in a tetrahydrofuran (THF)/dimethyl sulfoxide (DMSO)/water stream as summarized in Table 1. The crosslinking agent (tetraethylene pentamine, TEPA) at 0.5 equivalents with respect to charge groups on the poly(acrylic acid) was dissolved in the chloroform stream. Inverse nanoparticles (NPs) were produced with a confined impinging jet (CIJ) mixer to cause precipitation of the polysaccharide and collapse of the PAA block via rapid micromixing. Particle size characterization of the NPs was carried out by dynamic light scattering (DLS) using a Malvern Zetasizer ZS. By diluting the nanoparticle stream with dimethyl sulfoxide, the crosslinking extent was also be evaluated by DLS based on the correlation function strength and NP size change.

The polysaccharides were also encapsulated with different polystyrene block sizes of 15 k and 52 k weights. The formulations are not limited to those listed in Table 3, which is provided by way of example. For the 3 k MD, the loading has been varied from 40% to 95% with stable particles formed from 40% to 80% (polysaccharide per total weight solids). The water content has been varied from 0% to 10% in the DMSO stream and the total mass concentration has been varied from 7 mg/ml to 20 mg/ml. Additional compositions will produce NPs of tunable size.

Using a half-saturated brine solution to extract unencapsulated polysaccharide enabled determination of encapsulation efficiency (mass encapsulated/total mass of biologic added) for the formulations in Table 3. The encapsulation efficiency was greater than 97% for all. This excellent performance arises from the low solubility of sugars in chloroform. All samples have polydispersity less than 0.2, indicating low polydispersity, as summarized in Table 3.

Table 3: Summary of Inverse NPs of fluorescent polysaccharides. The polysaccharide concentration was 5 mg/ml.

TABLE 3

| Polysaccharide | Hydrophobic Block size | DMSO/THF/ Water % | PS-b-PAA (mg/ml) | NP size, nm (Polydispersity) | Encapsulation Efficiency |
|---|---|---|---|---|---|
| 1k MD | 5k PS | 50/45/5 | 5 | 61.7 ± 2.5 (0.10) | 97.8% |
| | 15k PS | 50/45/5 | 10 | 80.9 ± 4.6 (0.20) | 98.9% |
| | 52k PS | 50/47/2 | 15 | 65.7 ± 6.2 (0.17) | 99.3% |
| 3k MD | 5k PS | 50/45/5 | 5 | 63.8 ± 1.6 (0.07) | 97.4% |
| | 15k PS | 50/45/5 | 10 | 89.2 ± 4.3 (0.20) | 98.9% |
| | 52k PS | 50/47/2 | 15 | 61.4 ± 0.6 (0.11) | 99.4% |
| 20k Dex | 5k PS | 90/0/10 | 5 | 146.5 ± 3.1 (0.14) | 98.7% |
| | 15k PS | 80/10/10 | 10 | 155.7 ± 4.4 (0.14) | 98.8% |

An extraction-based assay was used to evaluate the impact of formulation parameters on rate of release from the inverse NPs. This process does not provide information about release as would be observed in vivo, but does provide insight for designing a formulation targeted to a given release rate. In this experiment, the inverse NPs were kept in a chloroform layer that was continually contacted with a brine layer on a rotary mixer. The polysaccharide concentration in the brine phase was monitored by fluorescence of AMC to track rate of loss from the NP core. Control experiments without stabilizing PS-b-PAA indicate that unecapsulated polysaccharide is immediately localized to the brine phase. So, any variation in the partitioning rate of the model biologic is due to the NP formulation. Release values below are normalized to the control experiment concentration in the brine phase to account for any solubility in chloroform and losses to mixer holdup.

Figure 7:
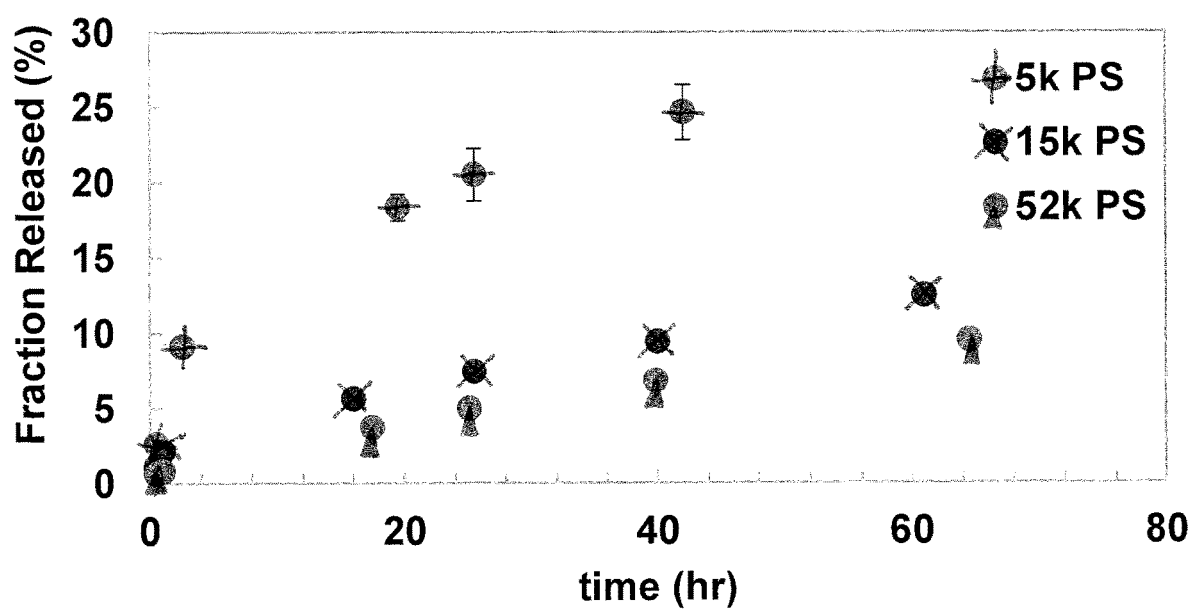
FIG. 7 is a graph showing the impact of hydrophobic block size on release rates for the 3 k MD (3275 g/mol maltodextrin) loaded (encapsulating) inverse nanoparticles with different hydrophobic block sizes (5 k PS, 15 k PS, and 52 k PS).
Figure 8A:
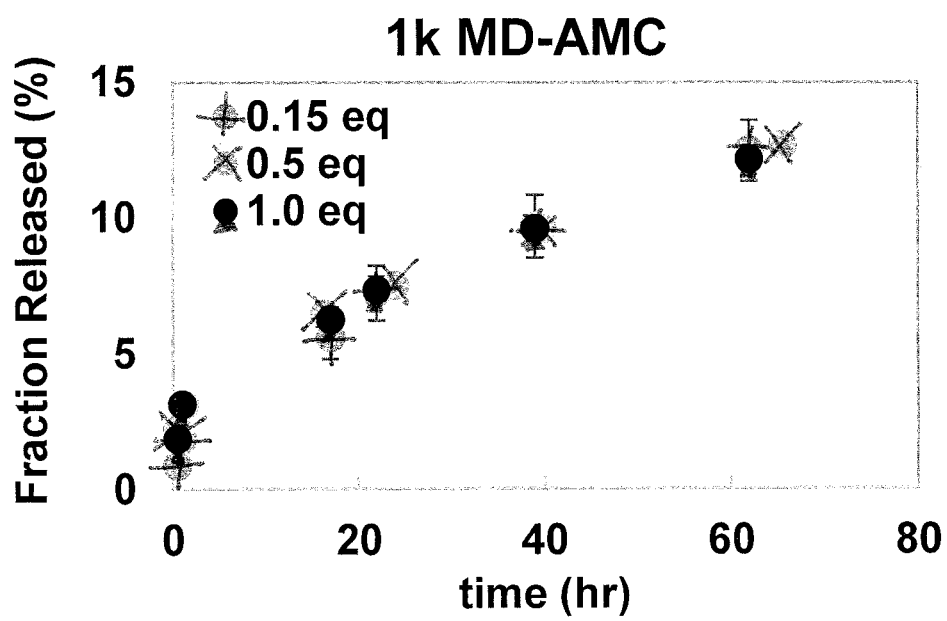
FIG. 8A is a graph showing the impact of crosslinking extent on release rate for the 1 k MD-AMC (1000 g/mol maltodextrin conjugated with 7-amino-4-methylcoumarin) loaded (encapsulating) inverse nanoparticles with different degrees of crosslinking; the inverse nanoparticles were formed from poly(styrene)-b-poly(acrylic acid), with the poly(styrene) (PS) block being 5000 g/mol molecular weight and the poly(acrylic acid) (PAA) block being 4800 g/mol molecular weight.
Figure 8B:
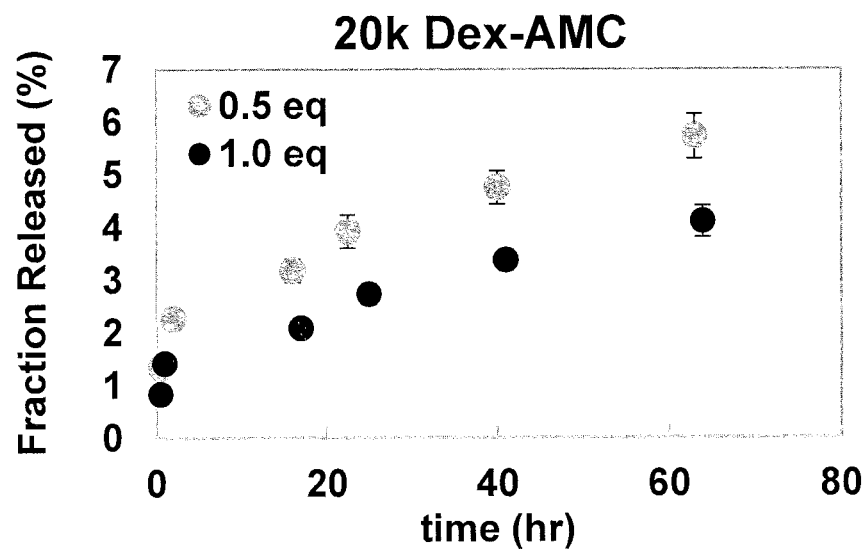
FIG. 8B is a graph showing the impact of crosslinking extent on release rate for the 20 k Dex-AMC (20,000 g/mol dextran conjugated with 7-amino-4-methylcoumarin) loaded (encapsulating) inverse nanoparticles with different degrees of crosslinking; the inverse nanoparticles were formed from poly(styrene)-b-poly(acrylic acid), with the poly(styrene) (PS) block being 5000 g/mol molecular weight and the poly(acrylic acid) (PAA) block being 4800 g/mol molecular weight.

FIG. 7 shows that larger PS block sizes slow release rates for 3 k MD-AMC. The same holds for all biologic sizes. This should be expected as the larger PS layer helps to maintain a steric barrier from the water interface and imposes a larger resistance on polysaccharide diffusion. However, above 15 k PS blocks, there is little benefit to increased molecular weight on extending the release profile.

FIG. 8A shows the impact of crosslinking extent on release rate for the 1 k MD-AMC (1000 g/mol maltodextrin conjugated with 7-amino-4-methylcoumarin) loaded (encapsulating) inverse nanoparticles with different degrees of crosslinking; the inverse nanoparticles were formed from poly(styrene)-b-poly(acrylic acid), with the poly(styrene) (PS) block being 5000 g/mol molecular weight and the poly(acrylic acid) (PAA) block being 4800 g/mol molecular weight. FIG. 8B shows the impact of crosslinking extent on release rate for the 20 k Dex-AMC (20,000 g/mol dextran conjugated with 7-amino-4-methylcoumarin) loaded (encapsulating) inverse nanoparticles with different degrees of crosslinking; the inverse nanoparticles were formed from poly(styrene)-b-poly(acrylic acid), with the poly(styrene) (PS) block being 5000 g/mol molecular weight and the poly(acrylic acid) (PAA) block being 4800 g/mol molecular weight. In FIGS. 8A and 8B, "Eq" represents equivalents of TEPA crosslinker with respect to acid groups on the PAA block. The crosslinking extent was found to have an impact on release rates for the largest model biologic (FIG. 8A) but not for the smallest (FIG. 8B). This suggests a diffusion-controlled release from the core where rates become reduced only as the mesh size approaches the diffusing species size. The release rate as a function of polysaccharide molecular weight was also studied. Overall, the slowest release is seen for 20 k Dex-AMC. However, the 1 k MD-AMC rate is slower than the 3 k MD-AMC. This may be due to the higher charge per mass of the 1 k versus the 3 k polysaccharide. A higher charge (due to the secondary amine linker to the fluorophore), would result in greater charge-charge interactions with the PAA core and slower release.

Example 13: Synthesis of Poly(Lactic Acid)-b-Poly (Aspartic Acid) and Poly(Lactic Acid)-b-Poly(Glutamic Acid) Block Copolymers for Inverse Nanoparticles A biocompatible and biodegradable stabilizing polymer is useful for biomedical applications of this invention. An example of such a polymer is poly(lactic acid)-b-poly(aspartic acid) (PLA-b-PAspA). Both blocks of this polymer are soluble in process solvents including dimethyl sulfoxide (DMSO) and dimethylformamide (DMF). Non-process solvents, including dichloromethane and chloroform, selectively precipitate the PAspA block and maintain the solubility of the PLA block. The acid groups on the PAspA provide functionalities through which the particles may be stabilized for further processing into aqueous media. For example, the PAspA may be crosslinked with metal cations such as Fe(III). The PLA-b-PAspA diblock-copolymer has been prepared as follows.

Scheme 1

(1)

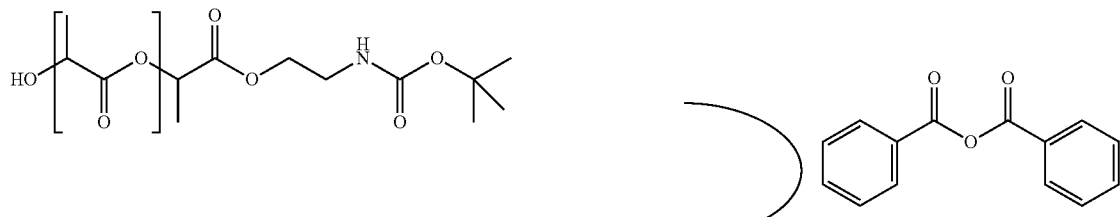

(2)

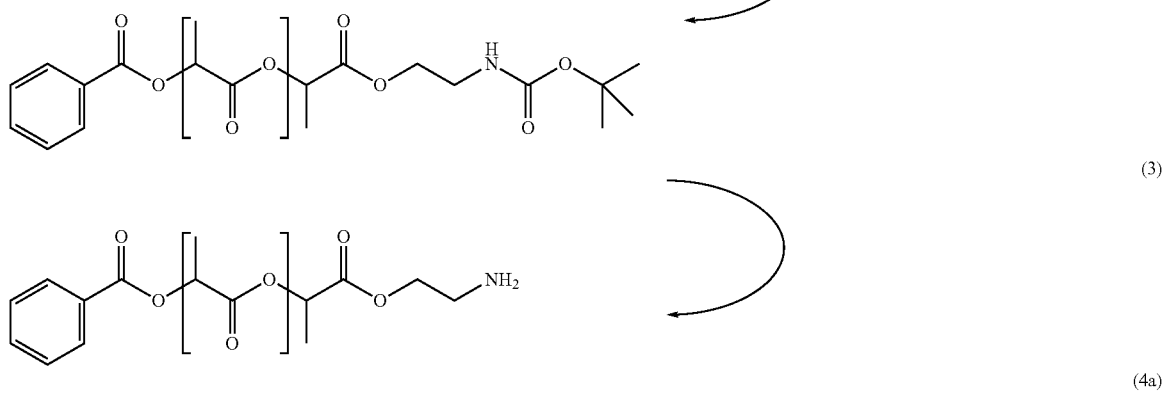

(3)

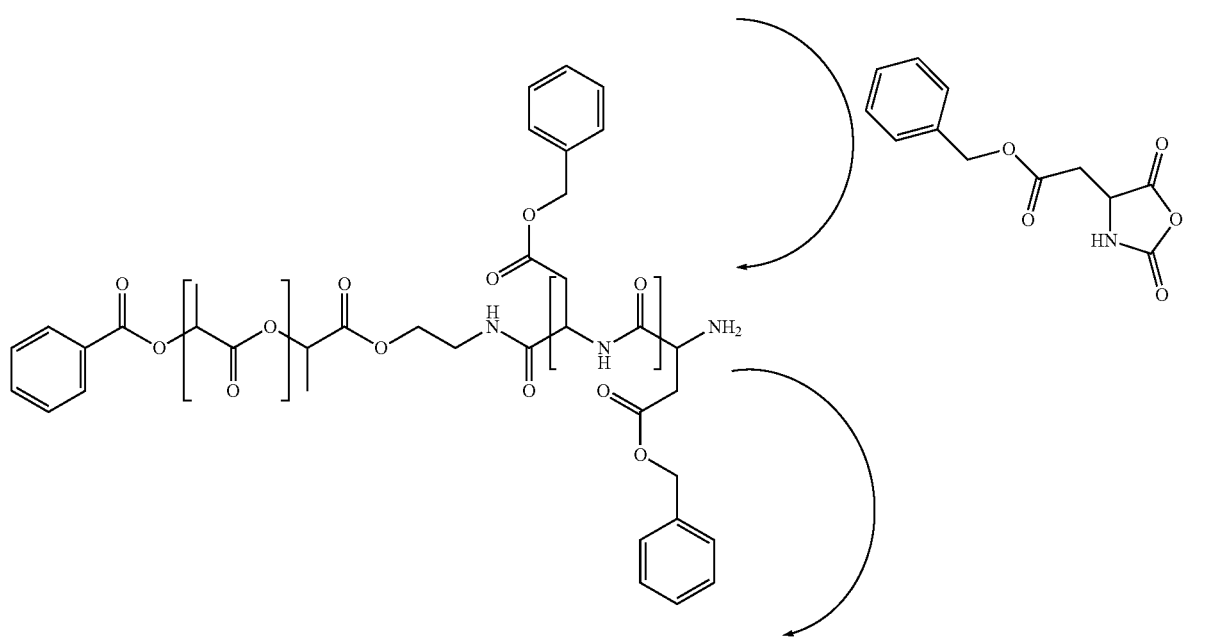

(4a)

(4b)

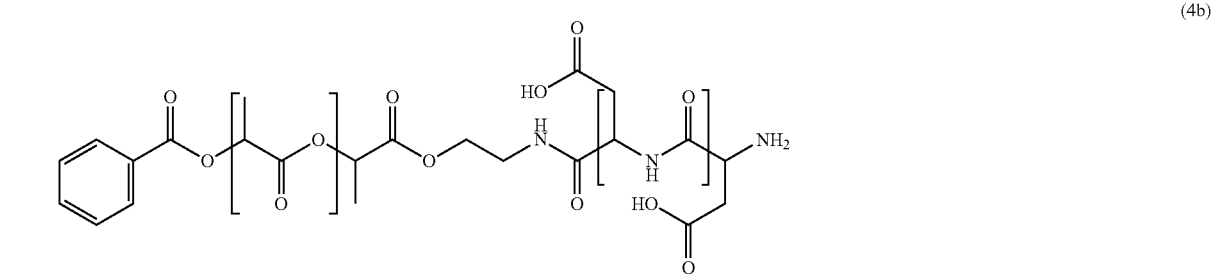

Lactide (17.3 mmole) and N-Boc-ethanolamine (0.45 mmole) were weighed into a dried round bottom flask and dried under high vacuum for 12 hours. Dimethylaminopyridine (DMAP, 0.45 mmole) was weighed into a separate flask and dried under high vacuum for 12 hours. Dry chloroform was added to each flask, and the DMAP was cannulated to the lactide flask to initiate the PLA polymerization at a lactide concentration of 1.5 M (Step 1, Scheme 1). The polymerization proceeded at 60° C. for three days. The resulting ~5 kDa polymer was precipitated into an excess of ice-cooled isopropyl alcohol, followed by two additional precipitations into dry-ice-cooled methanol. The resulting purified polymer was dried under high vacuum overnight.

The resulting hydroxyl-end of the HO-PLA-Boc was capped with benzoic anhydride (Step 2, Scheme 1). The HO-PLA-Boc was dissolved in dry dichloromethane with 3 molar equivalents of DMAP, 5 molar equivalents of trimethylamine, and 5 molar equivalents of benzoic anhydride at a polymer concentration of 50 mM. The reaction ran at room temperature for 12 hours, followed by precipitation into ice-cooled isopropyl alcohol, followed by two additional precipitations into dry-ice-cooled methanol. The resulting HO-PLA-Boc polymer was dried under high vacuum overnight.

The BOC group of the Bzl-PLA-Boc polymer was cleaved using trifluoroacetic acid (TFA) (Step 3, Scheme 1). The polymer was dried and dissolved in dry dichloromethane, and then TFA was added such that the final solution was 15 vol % TFA and 10 mM polymer. The reaction proceeded for 4 hours, then was precipitated into cold hexanes to remove the TFA. The polymer was then re-dissolved in dichloromethane with 10 molar equivalents of trimethylamine and mixed for 30 minutes to take the de-protected amine from its TFA-salt form into its free-base form. The Bzl-PLA-NH$_2$ polymer was precipitated into dry-ice cooled isopropyl alcohol (IPA) twice and dried under high vacuum overnight.

The second block of the di-block copolymer was grown using the Bzl-PLA-NH$_2$ as a macroinitiator (Step 4a, Scheme 1). The macroinitator (0.02 mmole) and O-Bzl protected N-carboxyanhydride monomer of aspartic acid (0.87 mmole) was dissolved in dry chloroform at an initiator concentration of 5 mM. The polymerization proceeded for 24 hours at 40° C., after which an equal volume of concentrated HBr in acetic acid was added to remove the O-Blz groups from the PAspA side chains (Step 4b, Scheme 1). The deprotection ran for 1 hour at room temperature, after which the polymer was precipitated into cold diethyl-ether three times. The resulting PLA$_{5kDa}$-b-PAspA$_{5kDa}$ polymer was dried under high vacuum overnight.

This synthetic scheme may be applied to the production of polymers with varying molecular weights and is not limited to the 5 kDa-block molecular weights described here. Additionally, the O-Bzl protected N-carboxyanhydride monomer of glutamic acid may be substituted for the aspartic acid monomer, resulting in poly(lactic acid)-b-poly(glutamic acid) (PLA-b-PGluA). PLA-b-PGluA may be used similarly to PLA-b-PAspA in the nanoparticle process.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A method for encapsulating a water soluble agent comprising:
    making an inverse nanoparticle dispersion by dissolving the water soluble agent in a first polar process solvent to form a water soluble agent solution,
    dissolving a copolymer in a second polar process solvent to form a copolymer solution,
    continuously mixing the water soluble agent solution and the copolymer solution with a nonprocess solvent to form a mixed solution from which inverse nanoparticles assemble to form an inverse nanoparticle dispersion, and
    aggregating the inverse nanoparticles to form microparticles or larger constructs to encapsulate the water soluble agent,
    wherein the copolymer comprises at least one region that is more polar and at least one region that is less polar,
    wherein the nonprocess solvent is less polar than the first polar process solvent,
    wherein the nonprocess solvent is less polar than the second polar process solvent,
    wherein the inverse nanoparticle comprises a core and a shell,
    wherein the core comprises the more polar region of the copolymer and the water soluble agent,
    wherein the shell comprises the less polar region of the copolymer, and
    wherein the mixing causes no more than 20 percent by volume of the first polar process solvent and the second polar process solvent to phase separate from the mixed solution.

2. The method of claim 1, wherein the water soluble agent is selected from the group consisting of a biologic material, an amino acid, a peptide, a protein, an antibody, DNA, RNA, mRNA, siRNA, a saccharide, glutathione, tryptophan, a lysozyme, glucagon-like peptide-I (GLP-I), a small molecule therapeutic, tobramycin, vancomycin, an imaging agent, eosin, eosin Y, tartrazine, a metal chelate, a gadolinium chelate, and gadolinium diethylene triamine pentaacetic acid (GD-DTPA).

3. The method of claim 1,
    wherein the at least one more polar region of the copolymer comprises at least one anionic more polar region and
    wherein the at least one anionic more polar region comprises poly(acrylic acid) (PAA), hyaluronic acid, poly(glutamic acid), poly(aspartic acid), or combinations.

4. The method of claim 1,
    wherein the at least one more polar region of the copolymer comprises at least one cationic more polar region and
    wherein the at least one cationic more polar region comprises chitosan, histadine lipids, histamines, spermadines, polyethylene-imines, lysines, arganines, histadine amino acids, or combinations.

5. The method of claim 1, wherein the at least one less polar region of the copolymer comprises poly(n-butyl acrylate) (PBA), poly(lactic acid) (PLA), poly(caprolactone) (PCL), poly(lactic-co-glycolic acid) (PLGA), poly(propylene sulfide) (PPS), a polyester, or combinations.

6. The method of claim 1, wherein the copolymer is poly(acrylic acid)-block-poly(n-butyl acrylate) (PAA-b-PBA).

7. The method of claim 1, wherein the copolymer is poly(aspartic acid)-block-poly(lactic acid).

8. The method of claim 7, further comprising
    adding a crosslinking agent to crosslink the copolymer,
    wherein the crosslinking agent is a metal cation.

9. The method of claim 7, further comprising
    adding a crosslinking agent to crosslink the copolymer,
    wherein the crosslinking agent is iron(III).

10. The method of claim 1, wherein the copolymer is poly(aspartic acid)-block-poly(caprolactone).

11. The method of claim 1, wherein the copolymer is a poly(aspartic acid)-block-poly(propylene sulfide) polymer.

12. The method of claim 1, wherein the first polar process solvent and the second polar process solvent are miscible.

13. The method of claim 1, wherein the first polar process solvent and the nonprocess solvent are miscible.

14. The method of claim 1, wherein the first polar process solvent and the nonprocess solvent are completely miscible at a ratio of a volume of the first polar process solvent to a volume of the nonprocess solvent used.

15. The method of claim 1, wherein the second polar process solvent and the nonprocess solvent are miscible.

16. The method of claim 1, wherein the water soluble agent solution is introduced as a first stream for continuous mixing with the nonprocess solvent.

17. The method of claim 1, wherein the first polar process solvent is the same as the second polar process solvent.

18. The method of claim 1, wherein the water soluble agent and the copolymer are both dissolved in a single polar process solvent to form a single solution, and the single solution is continuously mixed as a single stream with the nonprocess solvent to form the mixed solution from which the inverse nanoparticles assemble to form an inverse nanoparticle dispersion.

19. The method of claim 1, wherein the inverse nanoparticle has a size ranging from about 40 nm to about 900 nm.

20. The method of claim 1, further comprising stabilizing the inverse nanoparticle through crosslinking of the copolymer.

21. The method of claim 20, wherein the more polar region of the copolymer is crosslinked to stabilize the core of the inverse nanoparticle.

22. The method of claim 20, wherein the less polar region of the copolymer is crosslinked to stabilize the shell of the inverse nanoparticle.

23. The method of claim 20, wherein a crosslinking agent is added to crosslink a portion of the copolymer of anionic functionality and wherein the crosslinking agent is selected from the group consisting of an alkaline earth halide, a magnesium halide, magnesium chloride, a calcium halide, calcium chloride, a transition metal halide, an iron halide, iron(III) chloride, spermine, and combinations.

24. The method of claim 20, wherein a crosslinking agent is added to crosslink a portion of the copolymer of anionic functionality and wherein the crosslinking agent is selected from the group consisting of a metal acetate, an alkaline earth acetate, a transition metal acetate, and calcium acetate.

25. The method of claim 20, wherein a crosslinking agent is added to crosslink a portion of the copolymer of anionic functionality and wherein the crosslinking agent is chromium(III) acetate.

26. The method of claim 20, wherein the water soluble agent comprises tobramycin and wherein the tobramycin crosslinks the copolymer.

27. The method of claim 20, wherein the crosslinking agent is selected from the group consisting of polycitric acid, polyacrylic acid, polyaspartic acid, polyglutamic acid, multivalent anions, and combinations.

28. The method of claim 1,
wherein the inverse nanoparticle dispersion is in a nonpolar solvent phase, and
wherein the inverse nanoparticles are aggregated by emulsifying the nonpolar solvent phase in a polar external phase, and removing the nonpolar solvent to aggregate the nanoparticles to form microparticles.

29. The method of claim 28, wherein a compound, a lipid, and/or a polymer soluble in the nonpolar solvent phase is incorporated into the nonpolar phase as a glue molecule that aids in the formation of the microparticle.

30. The method of claim 28 wherein the polymer soluble in the nonpolar solvent phase is selected from the group consisting of poly(n-butyl acrylate) (PBA), poly(lactic acid) (PLA), poly(caprolactone) (PCL), poly(lactic-co-glycolic acid) (PLGA), poly(orthoester), poly(tyrosine), poly(propylene sulfide) (PPS), a polyester, and combinations.

31. The method of claim 28, wherein the microparticles are coated with a biocompatible agent and
wherein the biocompatible agent is introduced into the polar external phase used in the emulsification.

32. The method of claim 31, wherein the biocompatible agent is added to the nonpolar solvent phase during the emulsification, and migrates to the surface of the microparticle during aggregation.

33. The method of claim 1, wherein the inverse nanoparticles are aggregated by atomizing the inverse nanoparticle dispersion and drying the inverse nanoparticle dispersion during a spray drying step to form solid, essentially dry microparticles.

34. The method of claim 1, further comprising dissolving at least one crowder in the first polar process solution, the second polar process solution, and/or the nonprocess solvent.

35. The method of claim 34, wherein the at least one crowder is selected from the group consisting of glycerol, erythritol, arabinose, xylose, ribose, inositol, fructose, galactose, maltose, glucose, mannose, trehalose, sucrose, polyethylene glycol, an amino acid, peptide, an acrylate, carbomer 1342, a glucose polymer, a silicone polymer, polydimethylsiloxane, carboxy methyl cellulose, poly(glycolic acid), poly(lactic-co-glycolic acid), polylactic acid, dextran, a poloxamers, organic co-solvents selected from ethanol, N-methyl-2-pyrrolidone (NMP), PEG 300, PEG 400, PEG 200, PEG 3350, propylene glycol, N,N dimethylacetamide, dimethyl sulfoxide (DMSO), solketal, tetahydrofurfuryl alcohol, diglyme, ethyl lactate, a salt, a buffer, and combinations.

36. The method of claim 1,
wherein the copolymer is a triblock copolymer comprising blocks A, B, and C,
wherein the copolymer has the form A-B-C,
wherein block A is soluble in the second polar process solvent and is soluble in the nonprocess solvent,
wherein block B is insoluble in water and is soluble in the nonprocess solvent,
wherein block C is insoluble in the nonprocess solvent, and
wherein block C precipitates upon mixing of the water soluble agent solution, copolymer solution, and nonprocess solvent.

37. The method of claim 36,
wherein block A is poly(ethylene glycol) (PEG),
wherein block B is selected from the group consisting of poly(lactic acid) (PLA), poly(lactic-co-glycolic acid) (PLGA), poly(caprolactone) (PCL), and a polyester, and
wherein block C is selected from the group consisting of poly(acrylic acid), poly(aspartic acid), and poly(glutamic acid).

38. The method of claim 36, further comprising
adding a crosslinking agent to crosslink block C,
wherein block C is selected from the group consisting of poly(acrylic acid), poly(aspartic acid), and poly(glutamic acid) and
wherein the crosslinking agent is a metal cation.

39. The method of claim 38, wherein the metal cation is selected from the group consisting of an alkaline earth, magnesium (Mg), calcium (Ca), a transition metal, iron, and iron(111).

40. The method of claim 36, further comprising
adding a crosslinking agent to crosslink block C,
wherein block C is poly(glutamic acid) and
wherein the crosslinking agent is iron(III).

41. The method of claim 36, further comprising
combining the inverse nanoparticle dispersion with a reforming solvent,
wherein block A is soluble in the reforming solvent,
wherein block B is insoluble in the reforming solvent,
wherein following combination with the reforming solvent, the core of the inverse nanoparticle comprises block B and block C, and the shell of the inverse nanoparticle comprises block A.

42. The method of claim 41,
wherein block A is poly(ethylene glycol) PEG,
wherein block B is poly(lactic acid) (PLA), and
wherein the reforming solvent is water.

43. The method of claim 1,
wherein the copolymer is a diblock copolymer and
wherein the water soluble agent comprises a polysaccharide.

44. The method of claim 1, further comprising
adding a crosslinking agent to crosslink the copolymer,
wherein the copolymer is poly(acrylic acid)-b-poly(styrene) and
wherein the crosslinking agent is tetraethylene pentamine (TEPA).

45. The method of claim 1, wherein the copolymer is poly(glutamic acid)-b-poly(lactic acid).

* * * * *